United States Patent
Tsonton et al.

(10) Patent No.: US 7,438,692 B2
(45) Date of Patent: Oct. 21, 2008

(54) LOCALIZATION MECHANISM FOR AN MRI COMPATIBLE BIOPSY DEVICE

(76) Inventors: Mark Tsonton, 6802 Fairwind Ct., Loveland, OH (US) 45140; John C. Tinsley, III, 3518 Rawson Pl., Cincinnati, OH (US) 45209; Eric W. Thompson, 6577 Xenia Trail, Pleasant Plain, OH (US) 45162

( * ) Notice: Subject to any disclaimer, the term of this patent is extended or adjusted under 35 U.S.C. 154(b) by 494 days.

(21) Appl. No.: 10/273,445

(22) Filed: Oct. 18, 2002

(65) Prior Publication Data

US 2004/0077972 A1 Apr. 22, 2004

(51) Int. Cl.
*A61B 10/00* (2006.01)
(52) U.S. Cl. ...................................... 600/564
(58) Field of Classification Search ................. 600/564, 600/461, 407, 429, 439; 606/130
See application file for complete search history.

(56) References Cited

U.S. PATENT DOCUMENTS

| | | | |
|---|---|---|---|
| 4,875,478 A | 10/1989 | Chen | |
| 5,078,142 A * | 1/1992 | Siczek et al. | 600/407 |
| 5,409,497 A * | 4/1995 | Siczek et al. | 600/407 |
| 5,526,822 A | 6/1996 | Burbank et al. | |
| 5,560,373 A * | 10/1996 | De Santis | |
| 5,660,185 A | 8/1997 | Shmulewitz et al. | |
| 5,678,549 A | 10/1997 | Heywang-Koebrunner et al. | |
| 5,775,333 A | 7/1998 | Burbank et al. | |
| 5,776,062 A * | 7/1998 | Nields | 600/407 |
| 5,820,552 A * | 10/1998 | Crosby et al. | 600/407 |
| 5,830,219 A | 11/1998 | Bird et al. | |
| 5,855,554 A | 1/1999 | Schneider et al. | |
| 5,913,863 A | 6/1999 | Fischer et al. | |
| 6,022,325 A | 2/2000 | Siczek et al. | |
| 6,036,632 A | 3/2000 | Whitmore, III et al. | |
| 6,077,230 A | 6/2000 | Gregoire et al. | |
| 6,086,544 A | 7/2000 | Hibner et al. | |
| 6,110,112 A | 8/2000 | Heywang-Koebrunner | |
| 6,142,955 A | 11/2000 | Farascioni et al. | |
| 6,174,291 B1 | 1/2001 | McMahon et al. | |

(Continued)

FOREIGN PATENT DOCUMENTS

DE 19941019 C1 4/2001

(Continued)

OTHER PUBLICATIONS

RSNA Nov. 1999, vol. 213, p. 454 (#1521) The MR-Compatible Mammotome.

(Continued)

*Primary Examiner*—Max Hindenburg
*Assistant Examiner*—Fangemonique Smith
(74) *Attorney, Agent, or Firm*—Gerry Gressel

(57) ABSTRACT

A localization mechanism, or fixture, is used in conjunction with a breast coil for breast compression and for guiding a core biopsy instrument during prone stereotactic biopsy procedures in both open and closed Magnetic Resonance Imaging (MRI) machines. The localization fixture can include a breast compression plate and a biopsy probe support plate for supporting a biopsy probe for movement along multiple perpendicular axes. The position of both the breast compression plate and the biopsy probe support plate can be adjustable along an axis which is generally parallel to a probe needle.

3 Claims, 27 Drawing Sheets

U.S. PATENT DOCUMENTS

| | | | |
|---|---|---|---|
| 6,261,241 | B1 | 7/2001 | Burbank et al. |
| 6,261,299 | B1 * | 7/2001 | Chakeres |
| 6,270,506 | B1 | 8/2001 | Sittek et al. |
| 6,428,486 | B2 | 8/2002 | Ritchart et al. |
| 6,487,434 | B1 | 11/2002 | Kaiser et al. |
| 6,626,849 | B2 | 9/2003 | Huitema et al. |
| 6,638,235 | B2 * | 10/2003 | Miller et al. |
| 2001/0039378 | A1 * | 11/2001 | Lampman et al. |
| 2002/0016612 | A1 * | 2/2002 | Ashby et al. |
| 2002/0151820 | A1 | 10/2002 | Dvorak et al. |
| 2002/0156365 | A1 * | 10/2002 | Tsekos |
| 2003/0109801 | A1 | 6/2003 | Rhad et al. |
| 2003/0199753 | A1 * | 10/2003 | Hibner et al |
| 2003/0199754 | A1 * | 10/2003 | Hibner eta al. |
| 2003/0199785 | A1 | 10/2003 | Hibner et al. |

FOREIGN PATENT DOCUMENTS

| | | | |
|---|---|---|---|
| EP | 0995400 | A1 * | 4/2000 |
| EP | 1356774 | A1 * | 10/2003 |
| FR | 2332743 | A1 * | 11/1975 |
| WO | 0213709 | A1 | 2/2002 |

OTHER PUBLICATIONS

EPO Search Report dated Jan. 15, 2004 for related European Patent Application No. 03/256561.

* cited by examiner

LOCALIZATION MECHANISM FOR AN MRI COMPATIBLE BIOPSY DEVICE

CROSS REFERENCE TO RELATED APPLICATIONS

The present application cross references and incorporates by reference copending U.S. Ser. No. 10/171,330, "LOCALIZATION MECHANISM FOR AN MRI COMPATIBLE BIOPSY DEVICE" filed on Jun. 12, 2002, the disclosure of which is hereby incorporated by reference in their entirety.

FIELD OF THE INVENTION

The present invention relates, in general to devices for tissue sampling and, more particularly, to a device for positioning a biopsy probe with respect to a magnetic resonance imaging (MRI) device.

BACKGROUND OF THE INVENTION

The diagnosis and treatment of patients with cancerous tumors, pre-malignant conditions, and other disorders has long been an area of intense investigation. Non-invasive methods for examining tissue are palpation, Thermography, PET, SPECT, Nuclear imaging, X-ray, MRI, CT. and ultrasound imaging. When the physician suspects that tissue may contain cancerous cells, a biopsy may be done either in an open procedure or in a percutaneous procedure. For an open procedure, a scalpel is used by the surgeon to create a large incision in the tissue in order to provide direct viewing and access to the tissue mass of interest. Removal of the entire mass (excisional biopsy) or a part of the mass (incisional biopsy) is done. For a percutaneous biopsy, a needle-like instrument is used through a very small incision to access the tissue mass of interest and to obtain a tissue sample for a later examination and analysis. The advantages of the percutaneous method as compared to the open method are significant: less recovery time for the patient, less pain, less surgical time, lower cost, less risk of injury to adjacent bodily tissues such as nerves, and less disfigurement of the patient's anatomy. Use of the percutaneous method in combination with artificial imaging devices such as X-ray and ultrasound has resulted in highly reliable diagnoses and treatments.

Generally there are two ways to percutaneously obtain a portion of tissue from within the body, by aspiration or by core sampling. Aspiration of the tissue through a fine needle requires the tissue to be fragmented into small enough pieces to be withdrawn in a fluid medium. The method is less intrusive than other known sampling techniques, but one can only examine cells in the liquid (cytology) and not the cells and structure (pathology). In core sampling, a core or fragment of tissue is obtained for histologic examination, genetic tests, which may be done via a frozen or paraffin section. The type of biopsy used depends mainly on various factors present in the patient, and no single procedure is ideal for all cases. However, core biopsies seem to be more widely used by physicians.

Recently, core biopsy devices have been combined with imaging technology to better target the lesion. A number of these devices have been commercialized. One such commercially available product is marketed under the trademark name MAMMOTOME™, Ethicon Endo-Surgery, Inc. An embodiment of such a device is described in U.S. Pat. No. 5,526,822 issued to Burbank, et al., on Jun. 18, 1996, and is hereby incorporated herein by reference.

As seen from that reference, the instrument is a type of image-guided, percutaneous, coring, breast biopsy instrument. It is vacuum-assisted, and some of the steps for retrieving the tissue samples have been automated. The physician uses this device to "actively" capture (using the vacuum) the tissue prior to severing it from the body. This allows the sampling of tissues of varying hardness. The device can also be used to collect multiple samples in numerous positions about its longitudinal axis, and without removing the device from the body. These features allow for substantial sampling of large lesions and complete removal of small ones.

Co-pending application Ser. No. 09/825,899 filed on Apr. 2, 1997, which is hereby incorporated herein by reference, described other features and potential improvements to the device including a molded tissue cassette housing permitting the handling and viewing of multiple tissue samples without physical contact by the instrument operator. Another described therein is the interconnection of the housing to the piercing needle using a thumbwheel, to permit the needle to rotate relative to the housing, the preventing the vacuum tube from wrapping about the housing. During use, the thumbwheel is rotated so that the device rotates within the lesion, and samples can be taken at different points within the lesion.

In actual clinical use for breast biopsy the instrument (probe and driver assembly) is mounted to the three axis-positioning head of an x-ray imaging machine. The three axis-positioning heads is located in the area between the x-ray source and the image plate. The x-ray machines are outfitted with a computerized system which requires two x-ray images of the breast be taken with the x-ray source at two different positions in order for the computer to calculate x, y and z axis location of the suspect abnormality. In order to take the stereo x-ray images the x-ray source must be conveniently movable. The x-ray source therefore is typically mounted to an arm which, at the end opposite the x-ray source, is pivotally mounted to the frame of the machine in the region of the image plate.

Recently, there has been a need for a hand held core sampling biopsy device. This need has been fulfilled by Ethicon-Endo Surgery in U.S. Pat. 6,086,544 issued on Jul. 11, 2000, which is hereby incorporated herein by reference. This aforementioned patent discloses a hand held MAMMOTOME™ that may be held approximately parallel to the chest wall of the patient for obtaining tissue portions close to the chest wall than may be obtained when using an instrument that may be obtained when using an instrument that is mounted is manipulated by the operator's hand rather than by an electromechanical arm. Thus, the operator may steer the tip of the handpiece on the MAMMOTOME™ with great freedom towards the tissue mass of interest. The surgeon has tactile feedback while doing so and can thus ascertain to a significant, degree, the density and hardness of the tissue being encountered. In addition, a hand held MAMMOTOME™ is desirable because the handpiece on the MAMMOTOME™ may be held approximately parallel to the chest wall of the patient for obtaining tissue portions closer to the chest wall than may be obtained when using an instrument that is mounted to an electromechanical arm.

Recently, there has been a desire to use the above described biopsy devices with MRI imaging devices instead of x-ray imaging devices. However, existing medical biopsy sampling devices use small, multi-lumen probes extensively fabricated mostly if not entirely from metal. However, the ability to provide accurate minimally invasive diagnosis of suspicious breast lesions hinges on the size of the sample obtained and accuracy in placement of the sampling device.

The metallic nature of these probes has many drawbacks. Typically these metal probes are electrically conductive and often magnetically weak, which interferes with their use under MRI guidance. The electrically conductive and magnetically weak nature of metal probes often work to create field distortions, called artifacts, on the image. The image of the lesion will show the metal probe, and this is problematic because the image of the probe can obscure the image of the lesion.

The small sample size of conventional biopsy needles also presents a significant limitation due to the increase in the duration of the procedure. Due to the tendency for contrast agent to "wash out" suspicious lesions, and the progressive increase in enhancement of surrounding non-malignant breast parenchyma, suspicious lesions may become indistinguishable to the breast parenchyma within a few minutes. This limits the number of samples that can be retrieved using conventional spring-loaded core biopsy needles under direct imaging guidance.

A further problem not infrequently encountered during core needle biopsy is the development of a hematoma at the biopsy site during the procedure. An accumulating hematoma can be problematic during MRI-guided biopsy because residual contrast agent circulating in the hematoma can mimic enhancement in a suspicious lesion. In addition, the accumulation of air at the biopsy site can cause susceptibility artifacts that can potentially interfere with the fat-suppression MRI techniques at the biopsy site cavity.

These limitations of conventional biopsy needles have led several authors to conclude that lesions should be at least 1 cm in diameter before imaging could confirm that the MRI-guided biopsy device was definitely within (as opposed to adjacent to) the suspicious target. However, the demand for minimally invasive MRI-guided core biopsy is greatest for small lesions because they are more common, more difficult to characterize on MRI grounds alone, and have the best prognosis if they are found to be malignant.

Therefore, there has been a desire to have generally non-metallic (especially non-ferromagnetic) biopsy probe of the type described above to eliminate artifacts. These needs have been filled by co-pending and commonly-owned application Ser. No. 10/021680, "AN MRI COMPATIBLE SURGICAL BIOPSY DEVICE" to Huitema et al filed on Dec. 12, 2001, the disclosure of which is hereby incorporated by reference in its entirety. The lack of undesirable artifacts for the disclosed hand-held biopsy device allows the accurate placement of the probe. Moreover, disclosed vacuum assist allows visualization of the lesion entering a bowl of the probe to confirm accurate placement, as well as avoiding problems associated with a hematoma or an air cavity. Moreover, the volume and ability to rapidly rotate the open cutting bowl of the probe allows for multiple samples in succession without removal of the probe. Thereby, the duration of the procedure is reduced.

However, elimination of the artifact created by the metal probe entirely is also problematic because physicians rely extensively on some type of artifact to notify them as to where the tip of the probe is relative to the lesion. These needs have been filled by co-pending and commonly-owned application and Ser. No. 10/021407, entitled "AN MRI COMPATIBLE BIOPSY DEVICE HAVING A TIP WHICH LEAVES AN ARTIFACT" to Rhad et al., filed on Dec. 12, 2001, the disclosure of which is hereby incorporated by reference in their entirety. Having a target in the cutter at the distal end of the probe helps avoid advancing the probe through the chest cavity as well as accurately placing the bowl of the probe adjacent to the suspicious tissue for drawing into the cutting bowl.

While the aforementioned hand-held MRI compatible biopsy devices provide many advantages, opportunities exist for improvements and additional clinical functionality. For instance, the hand-held biopsy device presents a long, external handle that is inappropriate for closed magnet MRI machines. Furthermore, while the hand-held biopsy device allows great freedom in lateral and angular orientation, in some instances it is preferable to specifically position the biopsy probe. The MRI machine may provide very accurate stereotactic MRI-guided placement information that is only partially utilized in inserting the probe. In particular, the hand-held biopsy device is inserted through an opening in a compression plate, so some two-dimensional alignment is provided. However, the angle and depth of insertion the probe tends to vary, especially without continual reimaging of the probe during insertion, which is particularly inappropriate for closed MRI magnets.

Consequently, a significant need exists for a device for accurately positioning an MRI-assisted biopsy device.

BRIEF SUMMARY OF THE INVENTION

The invention provides an apparatus useful for positioning a biopsy probe.

In one embodiment the invention provides a localization apparatus for use in a medical compression apparatus for positioning a biopsy probe. The localization apparatus comprises a compression member containing a plurality of apertures, the position of the compression member being adjustable along an axis for providing tissue compression. At least two generally parallel, spaced apart supports extend in a direction generally parallel to the axis. The apparatus also includes a biopsy probe support, the position of which is adjustable along the two spaced apart supports. The biopsy probe support is adapted to support a biopsy probe between the two generally parallel spaced apart supports for movement of the biopsy probe in two directions perpendicular to the axis. The apparatus can further comprise at least two generally parallel spaced apart supports for supporting movement of the biopsy probe in a direction perpendicular to the axis.

In one embodiment, the invention provides a localization apparatus which includes a compression plate and a biopsy probe support plate. The compression plate can include a plurality of apertures sized and positioned to permit passage of a biopsy needle associated with the biopsy probe. The position of the compression plate can be adjustable for providing tissue compression. The biopsy probe support plate can extend generally parallel to the compression plate, and the biopsy probe support plate can be supported for movement relative to the compression plate. The biopsy support plate is adapted to support a biopsy probe assembly for movement in two mutually perpendicular directions (e.g. X and Z directions) which are transverse to the direction of movement of the biopsy support plate relative to the compression plate (e.g. Y direction).

The present invention also provides a localization apparatus comprising a compression member and a biopsy probe support, wherein the biopsy probe support is supported for movement with respect to the compression member, and wherein an apparatus associated with the biopsy probe support is adapted to releasably engage a biopsy probe assembly and position the biopsy probe assembly in two mutually perpendicular directions (e.g. X and Z directions) which are transverse to the direction of movement of the biopsy probe support relative to the compression member (e.g. Y direction).

DETAILED DESCRIPTION OF THE INVENTION

FIGS. 1 through 21 and the accompanying description are taken from the above referenced US Patent Application "Localization Mechanism for an MRI Compatible Biopsy Probe Device" Ser. No. 10/171,330 filed Jun. 12, 2002.

Figure 1:
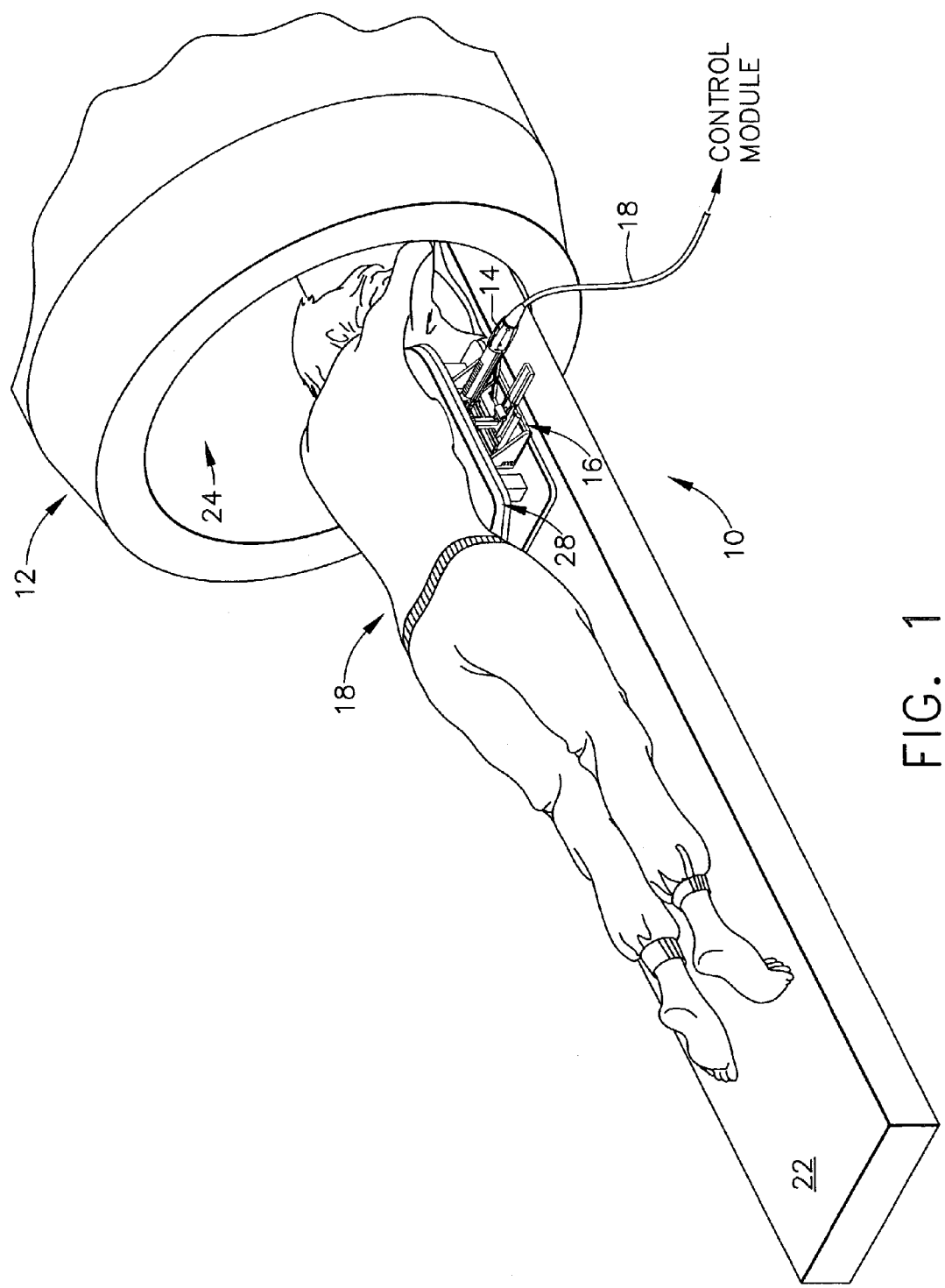
FIG. 1 is plan view of a biopsy instrument, mounting fixture, an Magnetic Resonance Imaging (MRI) breast coil fixture, and patient support table in working relationship outside the confines of an MRI machine.

FIG. 1 depicts a core biopsy instrument system 10 that is vacuum assisted, detachable, and compatible with use in a Magnetic Resonance Imaging (MRI) machine, such as the depicted closed MRI machine 12. In the illustrative embodiment, the core biopsy instrument system 10 includes an MRI-compatible biopsy tool 14 that is selectably attached to a localization mechanism or fixture 16 to accurately and rapidly perform core biopsies of breast tissue with a minimum of insertions of a biopsy probe. A control module (not shown) senses encoder position signal and switch signals from the biopsy tool 14 and provides mechanical and vacuum power to the biopsy tool 14 via power cord 18.

Figure 2:
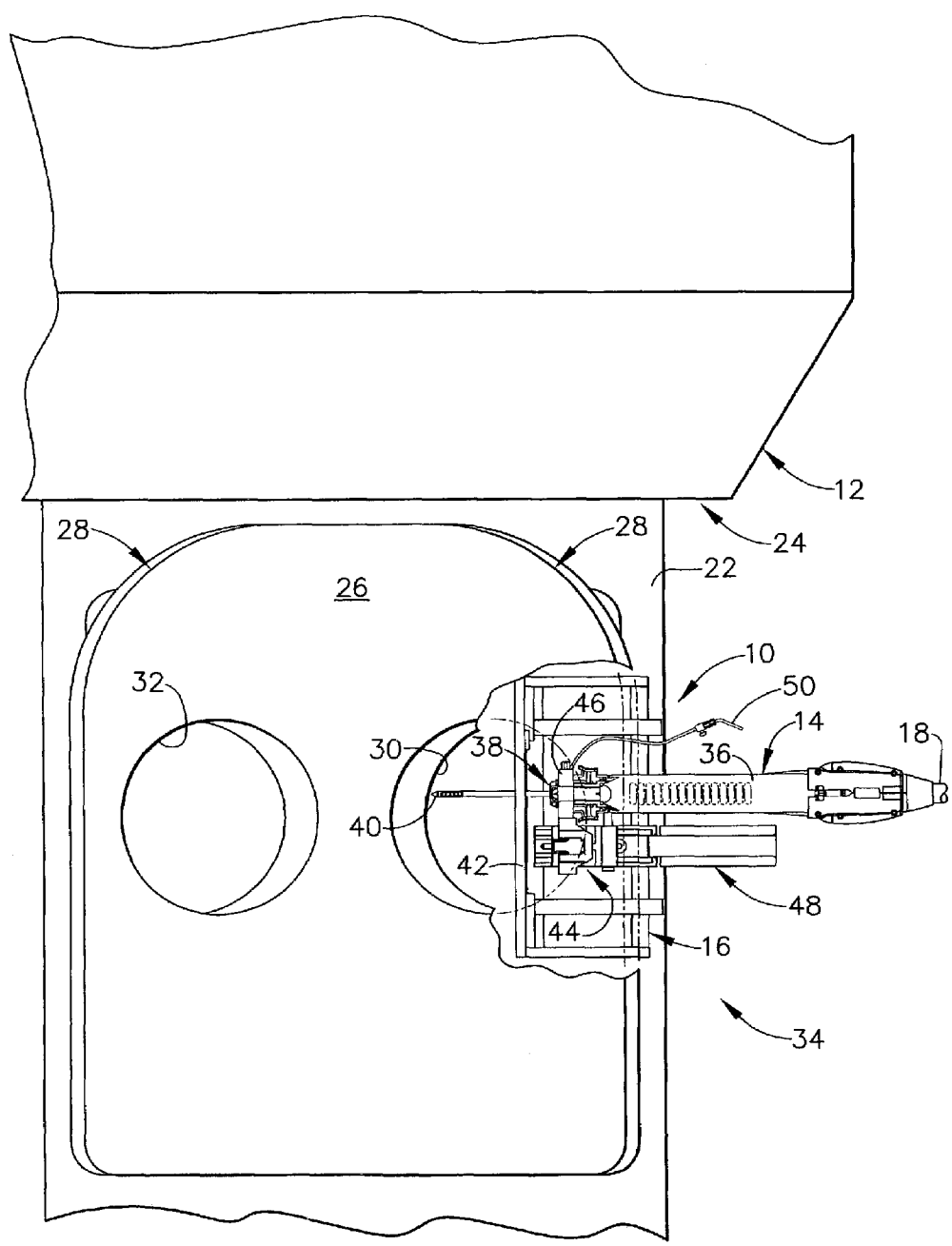
FIG. 2 is a plan view of a biopsy instrument, a localization fixture, partially cut away MRI breast coil fixture, patient support table, and in working relationship and configured for insertion into a MRI machine.

With reference to FIGS. 1-2, a patient 20 is lying prone upon a patient support table 22, depicted in FIG. 1 as removed from a magnet bore 24 of the MRI machine 12. The patient's chest rests upon a top surface 26 of a chest support 28, the top surface 24 having openings 30, 32 for allowing the patient's breasts to hang downward for imaging and treatment. With particular reference to FIG. 2, the right opening 30 is depicted with the localizer fixture 16 laterally positioned to cooperate with a medial compression plate (not shown) to longitudinally fix and compress the patient's right breast. Antenna elements (not shown) are placed about the opening 30 to detect radio frequency (RF) signals emanated from breast tissue induced by a strong magnetic field from the MRI bore 24. The chest support 28, localization fixture 16, and antennas are is generally termed a breast coil 34.

The biopsy tool 14 includes a biopsy handle 36 that attachable to a probe assembly 38. The localization fixture 16 accurately positions the probe assembly 38 for stereotactic MRI-guided biopsy procedures for a specific biopsy site location for a distal tip 40 of the probe assembly 38. This location is identified by an X-axis coordinate that is horizontal and longitudinal with respect to the patient (depicted as right to left in FIGS. 1-2). A Z-axis is defined as the vertical height, with the X and Z axis orthogonally defined on a lateral compression plate 42 of the localization fixture 16, the lateral compression plate 42 cooperating with the medial compression plate (not shown) to fix and compress the patient's breast. This location is also defined in terms of depth of insertion, or Y-axis, which is depicted as up and down in the FIGS. 1-2. A probe assembly mounting device 44 connects to a probe housing 46 of the biopsy tool 14.

The mounting device 44 includes alignment positioning guides (described in more detail below) to orient the probe housing 46, and hence the probe assembly 38, to the desired X-Y-Z coordinate. For instance, a depth slide 48 allows mounting of the probe assembly 38 with the distal tip 40 extends outside of the opening 30 and lateral compression plate 42. Thereafter, the probe assembly 38 is guided along the Y-axis by the depth slide 48 while maintaining the selected X-Z-axes coordinates. In addition, the mounting device 44 advantageously supports the biopsy handle 36 when attached to the probe assembly 38 as depicted in FIG. 2 to maintain the angle of insertion of the probe assembly 38. The probe housing 46 provides access to the interior of the probe assembly 38 via a vacuum lumen access conduit 50 for draining fluids, inserting fluids such as anesthetics.

Figure 3:
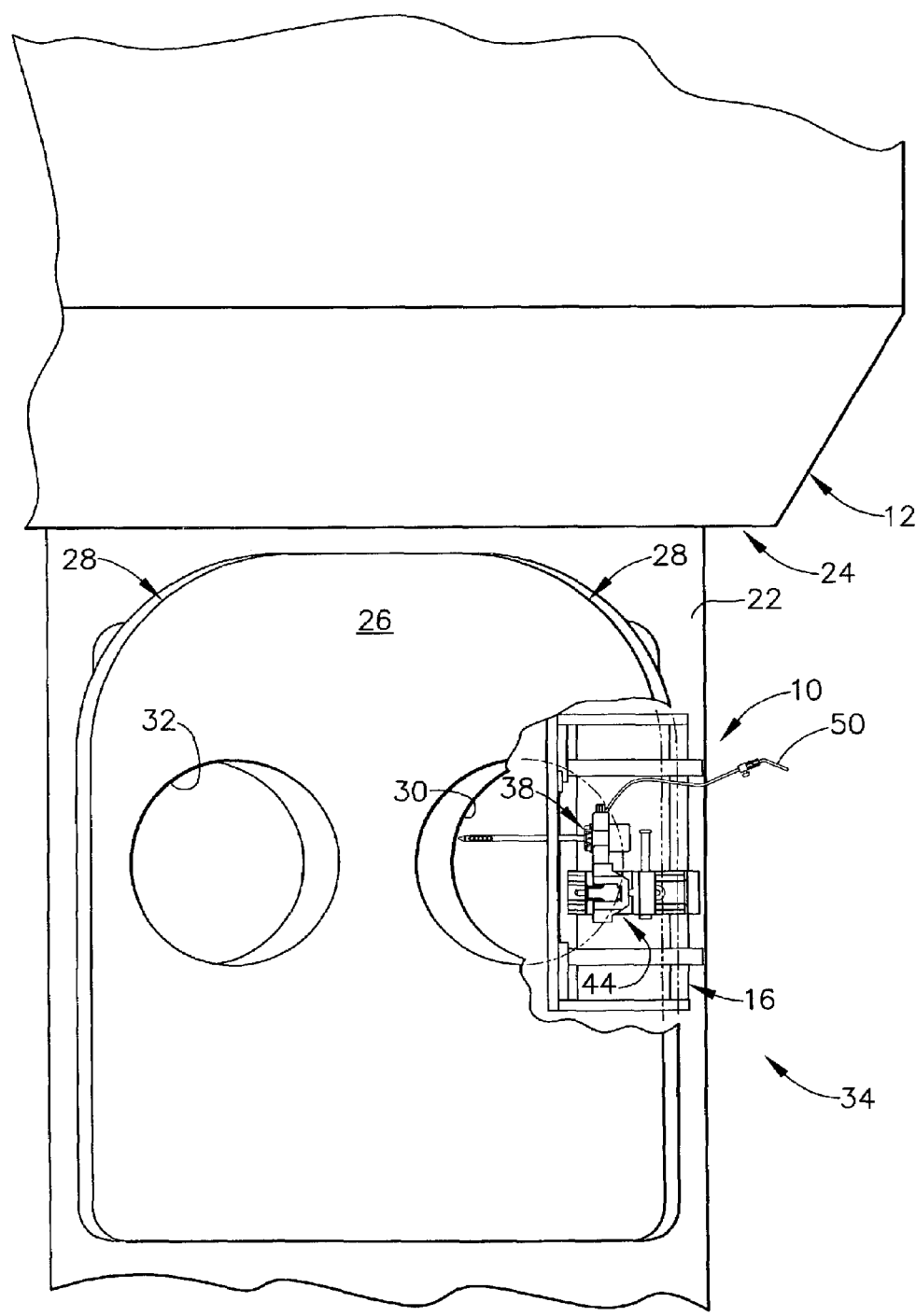
FIG. 3 is a plan view of a localization fixture, partially cut away MRI breast coil fixture, patient support table, and a detached probe assembly of the biopsy instrument mounted to the localization fixture, in working relationship and configured for insertion into the MRI machine.

FIG. 3 depicts the core biopsy instrument system 10 with the biopsy handle 36 removed and the depth slide 48 moved inward to allow insertion of the patient support table 22 into the narrow confines of the MRI magnet bore 24. Moreover, the surgeon may take full advantage of the stereotactic coordinates provided by the MRI machine 12, even if using a closed magnetic bore 24. In particular, the stereotactic derived coordinates may be used even if not actively imaging the probe assembly 38 during insertion. The localization fixture 16 enables the surgeon to manually insert the probe assembly 38 in depth with an indication of current depth. The surgeon is given tactile feedback while doing so and can thus ascertain to a significant degree the density and hardness of tissue being encountered. In addition, with the probe assembly 38 maintained in the correct location after insertion, the probe assembly 38 provides access for other diagnostic and therapeutic tools and fluid treatments.

Alternatively or in addition, a Y-axis adjustment mechanism may be incorporated into the localization fixture 16 to provide mechanical advantage, thereby achieving a controlled and deliberate insertion of the probe assembly 38. Moreover, the Y-axis adjustment mechanism may incorporate a frictional, ratcheting or locking feature to prevent inadvertent movement of the probe assembly 38 after placement at the desired biopsy location. Examples of such Y-axis adjustment include but are not limited to a thumb wheel in geared communication between the probe assembly mounting device 150 and the localizer support frame 126.

Figure 4:
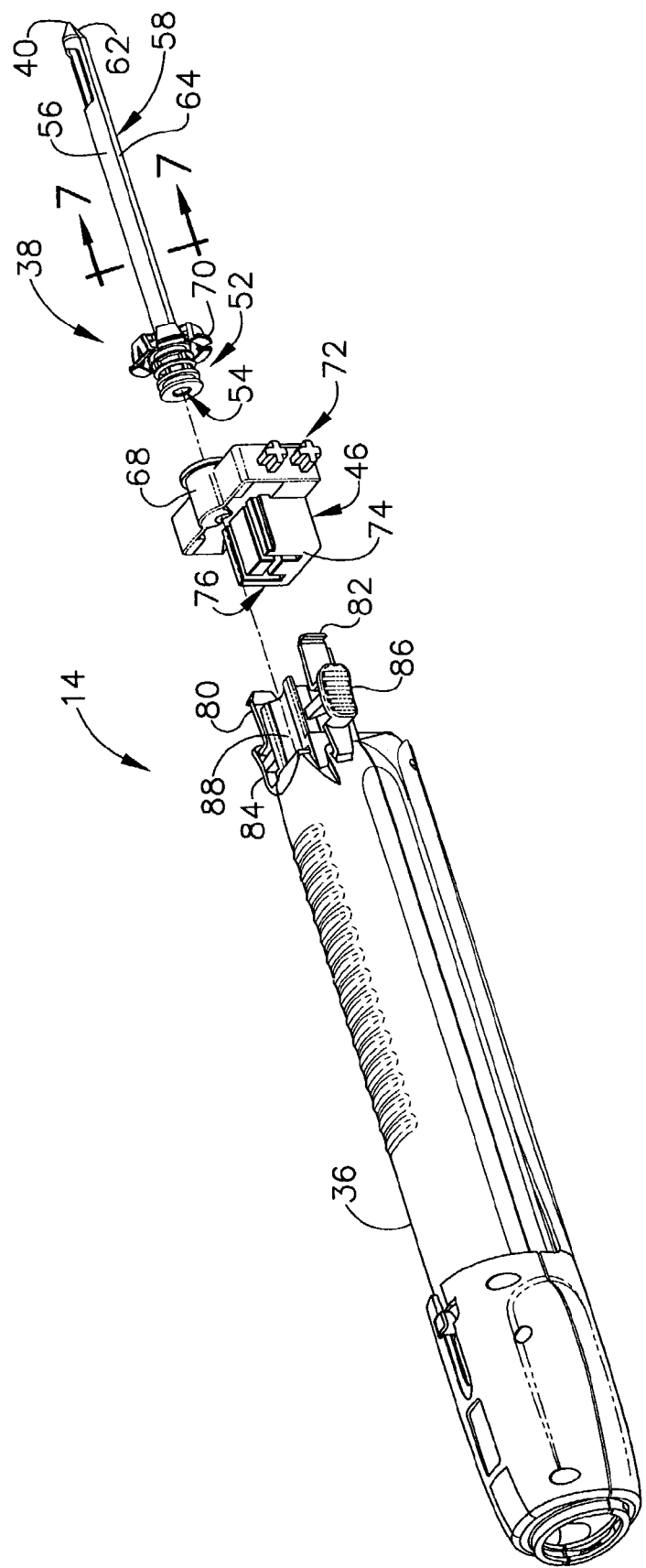
FIG. 4 is an isometric view of the biopsy instrument disassembled into a biopsy instrument handle, probe housing, and probe.

FIG. 4 depicts the biopsy tool 14 with the biopsy handle 36 depicted as readily attached to the probe housing 46, which in turn is readily attached to the probe assembly 38. The probe assembly 38 includes a male cylindrical mating portion 52 presenting a central cutter opening 54 on a proximal end that is aligned with the longitudinal length of a cutter lumen 56 of an elongated needle 58. The cutter lumen 56 communicates with a sample port 60 laterally presented near a needle tip 62 at the distal end of the needle 58. The needle tip 62 is for penetrating the soft tissue of a surgical patient. The needle tip 62 is sharpened and is preferably made from an MRI compatible resin such as ULTEM or VECTRA. In the illustrative embodiment, the needle tip 62 is a three-sided pyramidal shaped point, although the needle tip 62 configuration may also have other shapes and/or inserts. In addition, as in the aforementioned application Ser. No. 10/021407, entitled "AN MRI COMPATIBLE BIOPSY DEVICE HAVING A TIP WHICH LEAVES AN ARTIFACT", the illustrative embodiment advantageously includes a material that leaves a small, but not troublesome artifact on an MRI scan.

Figure 4A:
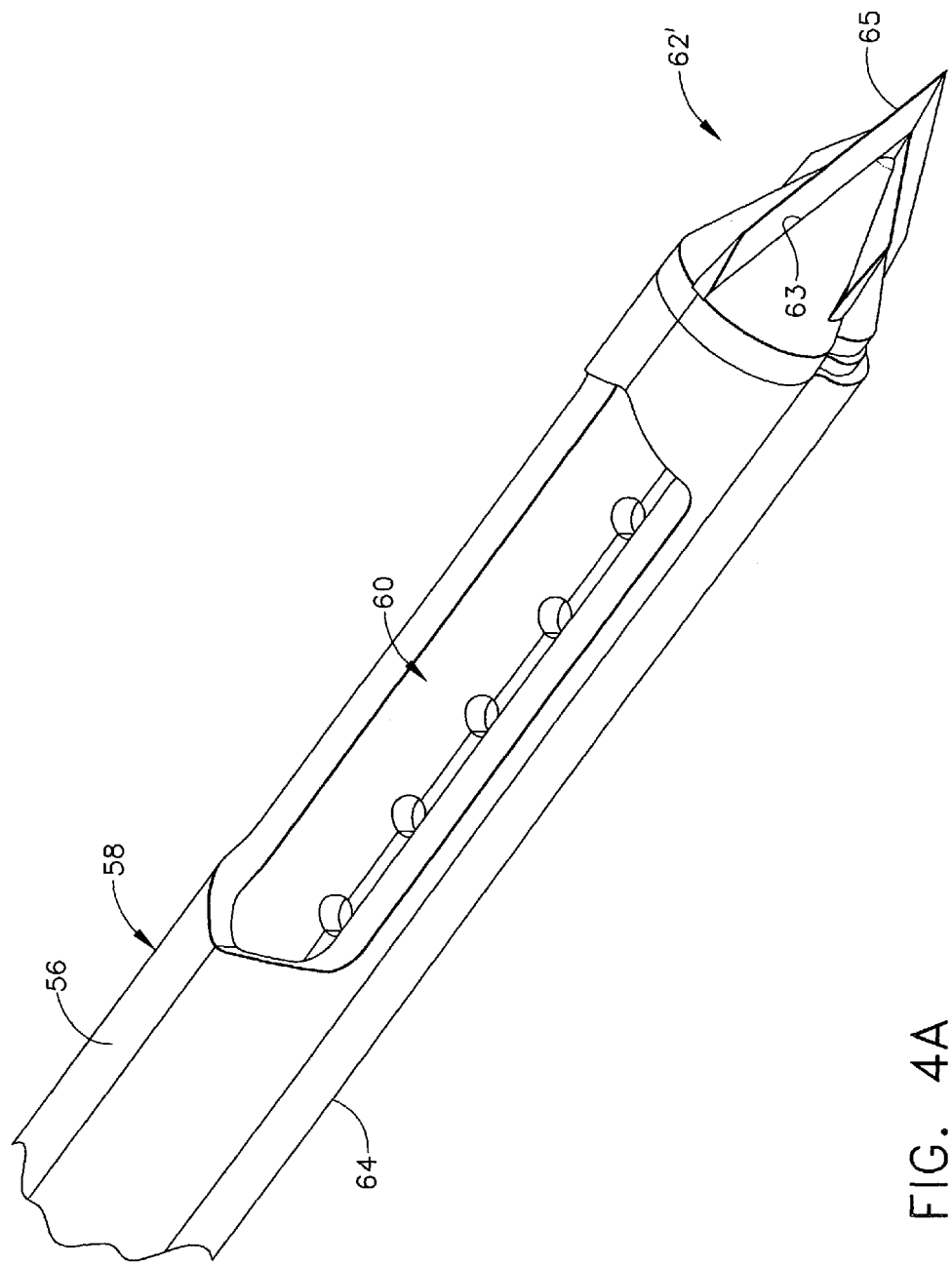
FIG. 4A is a frontal isometric detail view of an alternative needle tip of a biopsy instrument.

FIG. 4A depicts a needle tip 62' having a conical shape with a distally presented X-shaped slot 63 for receiving a pointed, sharpened blade 65 that reduces the probe insertion force into tissue. The blade 65 could be made of titanium, stainless steel, nitinol, aluminum, Elgiloy, ceramic, etc. It will be appreciated that other shapes of sharpened blade 65 may be used, such as a single pointed surface in a distally presented single slot rather than two perpendicularly crossed, pointed surfaces as depicted.

It will be appreciated that a cutter element or an obturator stylet is advanced inside the cutter lumen 56 to block the sample port 60 during insertion. Once the needle 58 is positioned, the sample port 60 is exposed to allow tissue to enter. In particular, a vacuum may be presented to a "sample bowl" inside the cutter lumen 56 near the sample port 60 by applying vacuum power through a vacuum chamber lumen 64 that communicates along the longitudinal length of the needle 58 to the male cylindrical mating portion 52. In particular, a series of small holes allow gas and fluid to enter the vacuum chamber lumen 64 from the sample port 60 but prevent tissue samples from entering.

Annular rings 66 about the cylindrical mating portion 52 grip and seal to an interior of a female cylindrical mating portion 68 on the probe housing 46. Between annular rings, a proximal vacuum port (not shown in FIG. 4) communicates with a vacuum passage (not shown) in the probe housing 46. The engagement between the mating portions 52, 68 advantageously allows rotation of the needle 58 with a thumb wheel 70 annularly presented near the proximal end of the needle 58. The radial opening presented by the annual rings 66 maintains communication between the vacuum passage in the probe housing 46 and the vacuum chamber lumen 64 regardless of radial orientation of the needle 58. Thereby, the sample port 60 may be presented to tissue at any and all radial positions about the distal end of the needle 58. With the assistance of vacuum, a large volume of tissue may be selectably drawn into the sample bowl for biopsy sampling.

The probe housing 46 includes laterally presented attachment prongs 72 for mounting to the localization fixture 16. In addition, the probe housing 46 presents a proximally directed cuboidal engagement member 74 with longitudinally aligned vertical and horizontal grooves 76 for flanges 78 from the biopsy handle 36. The probe housing 46 also receives hooked locking tabs 80, 82 on the distal engaging end of the biopsy handle 36 for selective locking and unlocking under the influence of a pair of opposing depression grips 84, 86 attached to respective tabs 80, 82. The biopsy handle 36 includes a sample window 88 for extracting any tissue sample withdrawn from the cutter lumen 52 under the influence of a vacuum passing through the cutter, as described in more detail below.

Figure 5:
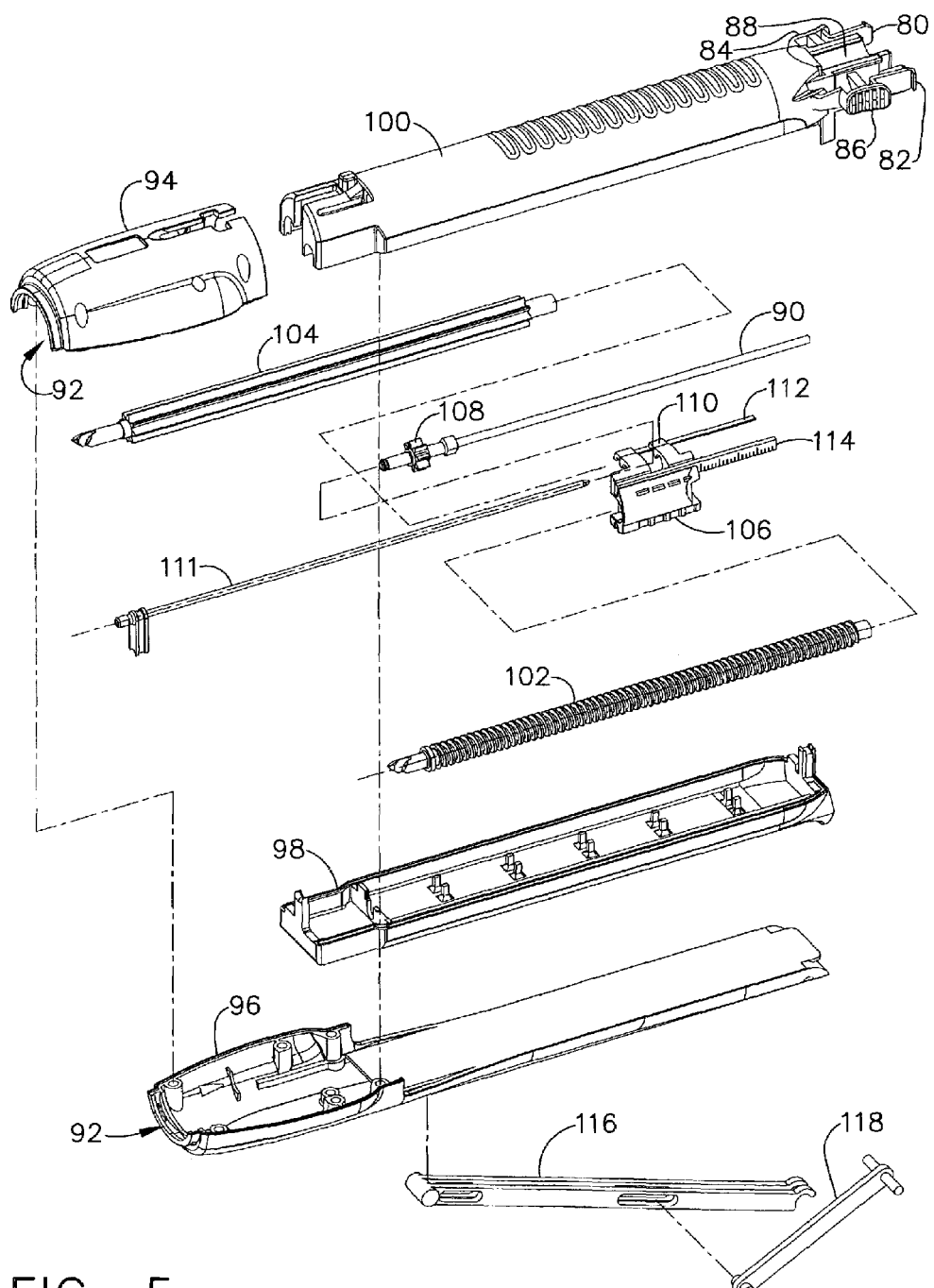
FIG. 5 is an exploded isometric view of a biopsy instrument handle.

FIG. 5 depicts a disassembled biopsy handle 36 that contains the means for translating and rotating a cutter 90 within the cutter lumen 56. It will be appreciated that two rotating mechanical power sources are presented to the proximal end of the biopsy handle 36 through the power cord 18 to provide the independent translation and rotation motions. These two rotating mechanical power sources enter through a cord opening 92 defined between a removable shell 94 and a bottom shell 96, the two held together by screws. The removable shell 94 is removed when assembling a power cord 18 to the handle 36. A lower gear housing 98 is supported upon the bottom shell 96 and cooperates with a top shell 100 to constrain movement of an elongate drive screw 102, an elongate axial screw 104 and cutter carriage 106. In particular, both screws 102, 104 are allowed to rotate, positioned parallel to one another and the longitudinal axis of the cutter lumen 56. Each screw 102, 104 is driven by a respective power source from the power cord 18. The drive screw 102 passes through the carriage 106 and interacts with corresponding ridges therein to impart a longitudinal translation corresponding to the direction and rate of rotation of the drive screw 102.

In some applications, a single rotary power source may be used as an alternative to two independent rotating mechanical power sources. A transmission mechanism at the biopsy handle 36 may convert the single rotary power source into the two motions, translation and rotation. As yet another alternative, the single rotary power source may directly supply both a translation and rotary motion. Such a translating and rotating power cable would be coupled to the cutter 90 to directly control its movement.

The cutter 90 is an elongate tube with a sharpened distal end for cutting tissue presented within the distal end of the cutter lumen 56. The proximal end of the cutter 90 includes a cutter gear 108 that is exposed through a gear window 110 of the carriage 106 to mesh with the axial screw 104 for axial rotation of the cutter 90. A tissue remover 111 is a tube that is fixedly aligned with the longitudinal axis to enter the proximal end of the cutter 90. The tissue remover 111 extends up to the sample window 88 and has a vacuum selectably applied to it by the control module. Thus, when the cutter 90 is retracted, vacuum from the tissue remover 111 draws the sample to the distal end of the cutter 90 for retraction to the sample window 88, whereupon the sample encounter the tissue remover 111 and is dislodged for exiting the biopsy tool 14.

The carriage 106 includes distally projected guides 112, 114 that advantageously take-out slack between biopsy handle 36 and the probe housing 46, as well as providing indicia to the surgeon as to the depth of translation of the cutter 90. Taking out slack between the assembled parts of the handle 36 and housing 46 advantageously minimizes the deadzone length of the distal end of the needle 58. The cutter 90 should completely translate past the sample port 60 in order to reliably cut a sample. To ensure a full cut, the cutter 90 should translate the maximum distance expected for the assembly. If variation exists in manufacturing tolerances between the engagement components, then a further distance has to be included in the cutter lumen 56 distal to the sample port 60 to accommodate the over-travel. Thereby, the needle tip 62 must be advanced farther than desirable in some instances, preventing placement of the sample port 60 near critical body tissues. At or near full travel, the guides 112, 114 contact the probe housing 46, causing movement of the housing 46 to its maximum, distal position. Thus, critical dimensioning to minimize tolerance build-up is simplified.

FIG. 5 also depicts a brace 116 and brace arm 118 that are employed in one version of the localization fixture 16 to support the weight and maintain the alignment of the handle 36. Thereby, flexure of the assembly is avoided that may place a load on the probe assembly 38, and thus unwanted movement of the needle 58 from the desired biopsy site location.

Figures 6, 7:
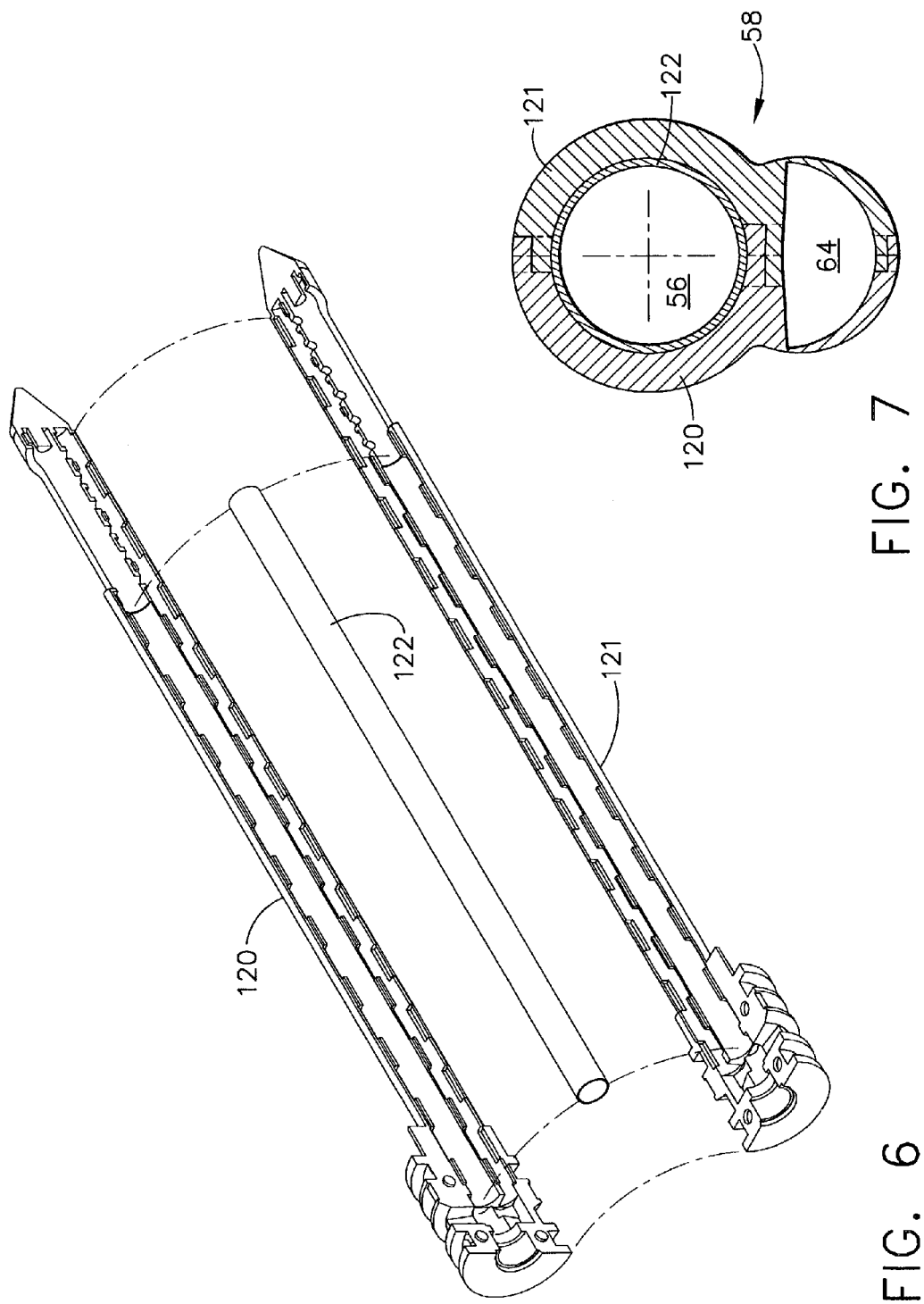
FIG. 6 is an exploded isometric view of the probe of the biopsy instrument of FIG. 4.
FIG. 7 is a transverse cross section of the probe of the biopsy instrument of FIG. 4 along lines 7-7.

FIGS. 6-7 depict the needle 58 of FIG. 4 and described more fully in the aforementioned application Ser. No. 10/021680, entitled "AN MRI COMPATIBLE SURGICAL BIOPSY DEVICE". In particular, elongated needle 58 is formed from a left body member 120 and a right body member 121 on either side of the longitudinal axis. The edges of the halves 120 and 121 are gated for easy part filling, and the edges are stepped with ridges that allow the two halves 120 and 121 to attach together with ease. The two halves 120, 121 are adhesively attached to one another. A cutter tube liner 122 is inserted between the two halves 120, 121 to provide a smooth surface for the cutter 90, especially by preventing adhesive from entering the cutter lumen 56 during assembly.

Figure 8:
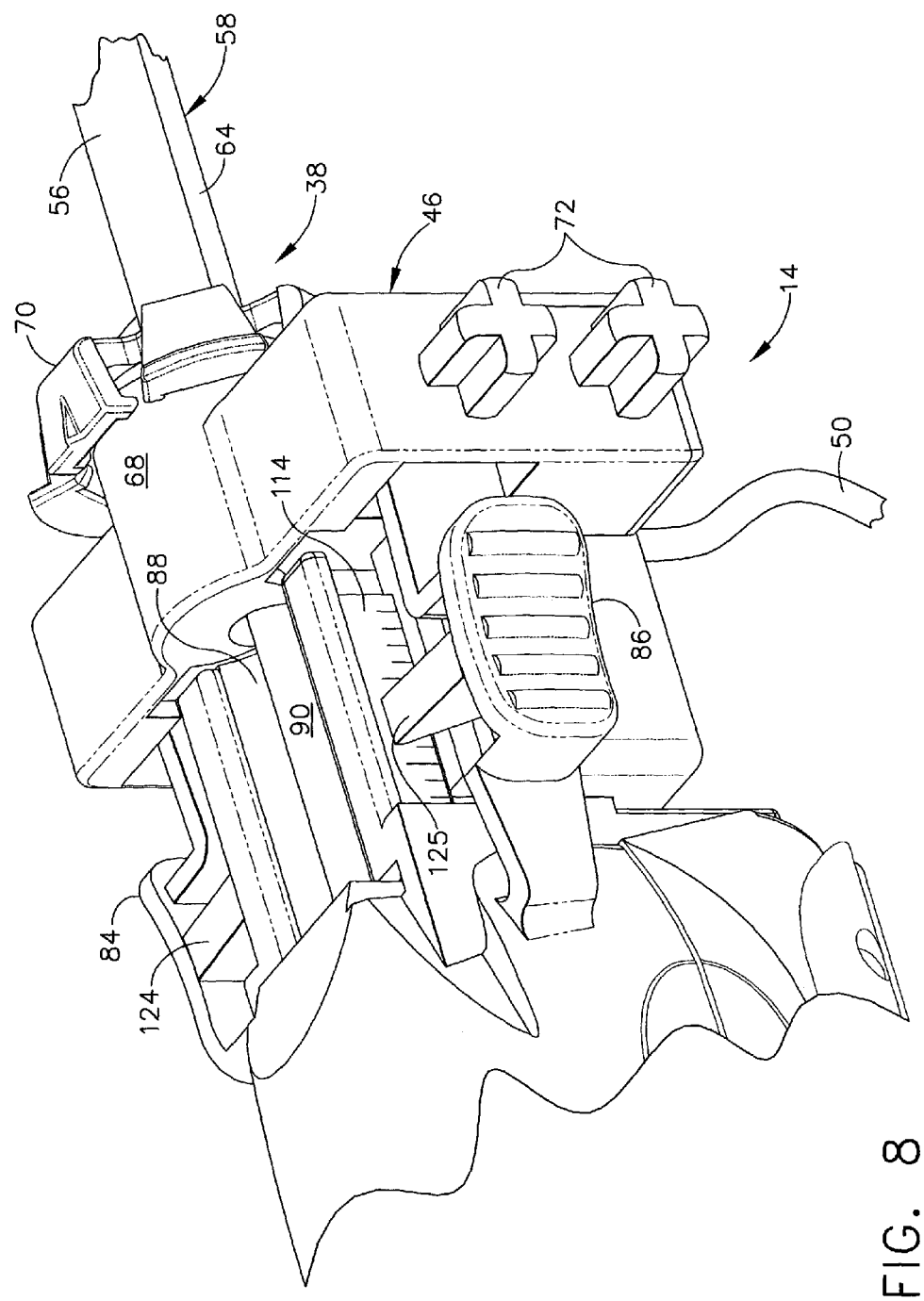
FIG. 8 is an enlarged isometric view of the interface between the handle and probe housing illustrating the visual confirmation elements that indicate the position of the distal end of the cutter.

FIG. 8 shows an enlarged view of the engagement of the handle 36 to the probe housing 46, with the advanced cutter 90 evident through the window 88. In addition, the guides 112, 114 are advanced almost into contact with the probe housing 46, indicating that the distal end of the cutter 90 is approaching its furthest translation. The guides 112, 114 contact the probe housing 90 when at or near this extreme to take-out any tolerance.

Indicia on the side of the guides 112, 114 may be referenced by the surgeon to determine the position of the cutter. Also shown in more detail is hooked locking tabs 80, 82 entering the probe housing 46, the thumb wheel 70 used to rotate the needle 80, and the vacuum lumen access conduit 50 used to evacuate or otherwise access the vacuum lumen 64.

Figure 9:
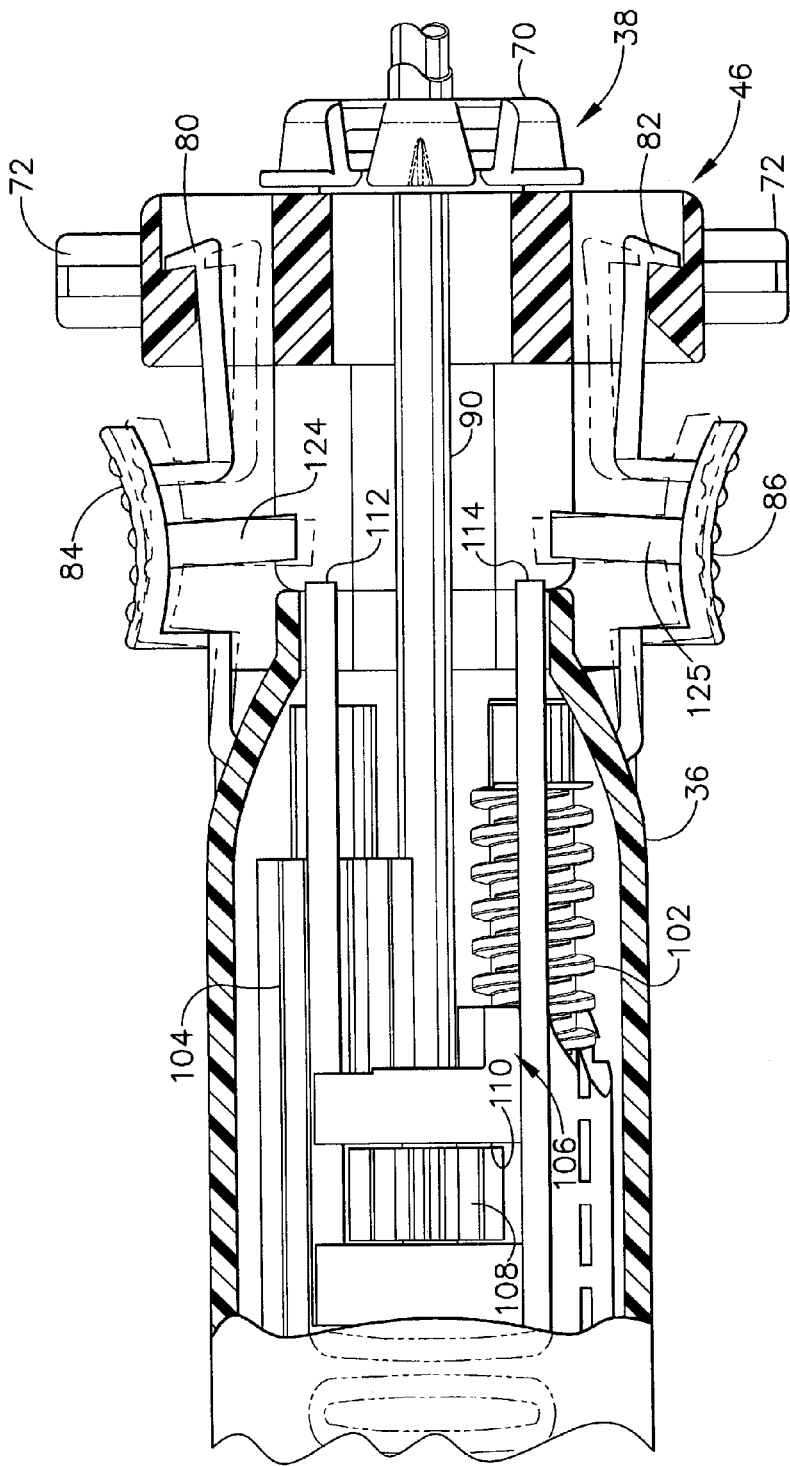
FIG. 9 is a fragmentary plan view in partial section of the distal portion of the handle and probe housing and assembly, illustrating the disconnect feature with the cutter retracted.
Figure 10:
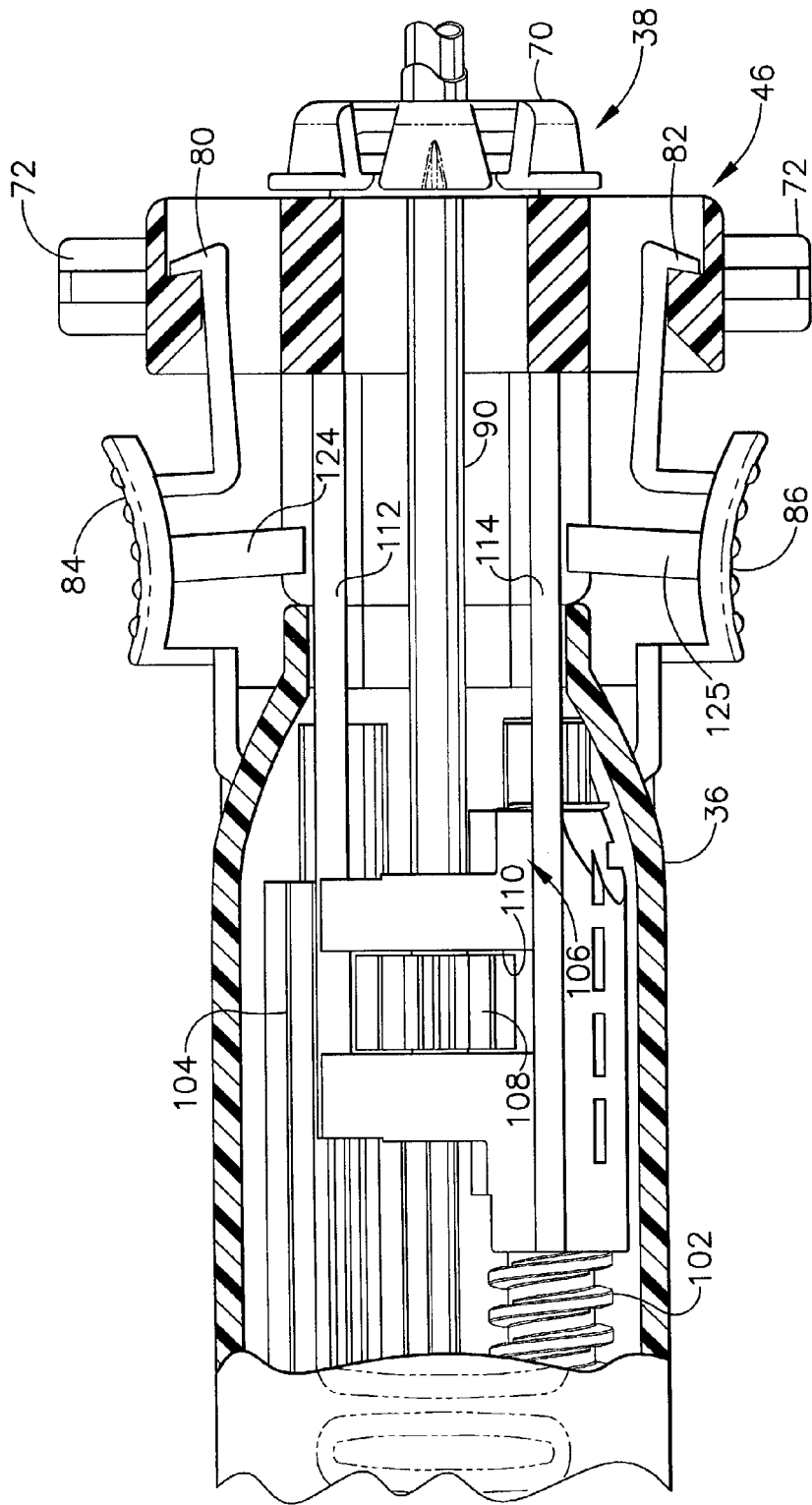
FIG. 10 is a fragmentary plan view in partial section of the distal portion of the handle and probe housing and assembly, illustrating the tolerance take-out feature and the disabled disconnect feature when the cutter is advanced.

FIGS. 8-10 show that each grip 84, 86 includes a respective inwardly projecting member 124, 125 that contact the guides 112, 114 when the cutter 90 is distally advanced, thereby preventing removal of the handle 36. In FIG. 9, the cutter 90 is retracted, allowed the depression of the grips 84, 86, unlocking the hooked locking tabs 80, 82 from the probe housing 46. In FIG. 10, cutter carriage 106 is advanced, the guides 112, 114 are contacting the probe housing 46, thereby removing any longitudinal gap between the hooked locking tabs 80, 86 and the probe housing 46.

FIGS. 11-14 depicts a localization fixture 16 that includes means for accurately positioning the probe assembly 38 and supporting the biopsy handle 36. In particular, a localizer support frame 126 is formed from the compression plate 42 in a hinged, orthogonal relation to a horizontal slide plate 128, both laterally attached to one another by gussets 130, 132. Rods 134, 136 horizontally pass through the compression plate to adjustably attach to the medial compression plate (not shown) for compressing the patient's breast. Apertures, depicted as parallel rows of slots 138, in the compression plate 42 are provided to obtain access to a desired biopsy site location while providing enough remaining structure in the compression plate 42 for adequate contact with the patient's breast. Alternatively, the apertures may be a series of holes aligned both vertically and vertically, parallel columns of slots, or a large opening of other shapes. As yet a further alternative, portions of the compression plate 42 may be permeable to allow an aperture to be formed as needed.

The desired biopsy site location is stereotactically determined during an MRI scan with reference to a fiducial marker 140 that presents a small artifact. The fiducial marker 140 is contained within a fiducial marker holder 142 that may be placed at a convenient location on the compression plate 42, accurately placed with reference to indents spaced along the slots 138. Alternatively, the fiducial marker may be embedded or affixed to the compression plate 42.

The localizer support frame 126 defines and provides the guide for positioning the probe assembly 38. The X-Y-Z axes are defined with regard to the slots 138 and compression plate 42. In particular, the vertical dimension, or Z-axis, and horizontal dimension, or X-axis, are defined by the surface of the compression plate 42. The depth dimension, or Y-axis, is defined as distance away from the plane of the compression plate 42. The horizontal slide plate 128 includes laterally aligned front and back rails 144, 146 for setting the X-axis coordinate. Horizontal indicia 148 along the front rail 144 give the surgeon an accurate measurement of the position of a probe assembly mounting device 150.

A first version of the mounting device 150 is depicted that uses a single vertical pedestal 152 to position and support the probe assembly 38. In addition, the biopsy handle 36 is supported by a brace 116 connected to the proximal underside of the handle 36 to a handle support rod 156 that is slid through a rod hole 158 to the corresponding side of the vertical pedestal 152. The appropriate height for the brace 116 is determined by selecting one of a range of slots arrayed along the underside of the handle, thereby pivoting the brace 116 about a brace arm 118 whose first end slidably pivots within a slot 162 in the middle of the brace 116 and second end attaches to the distal end of the handle 36.

Figure 11:
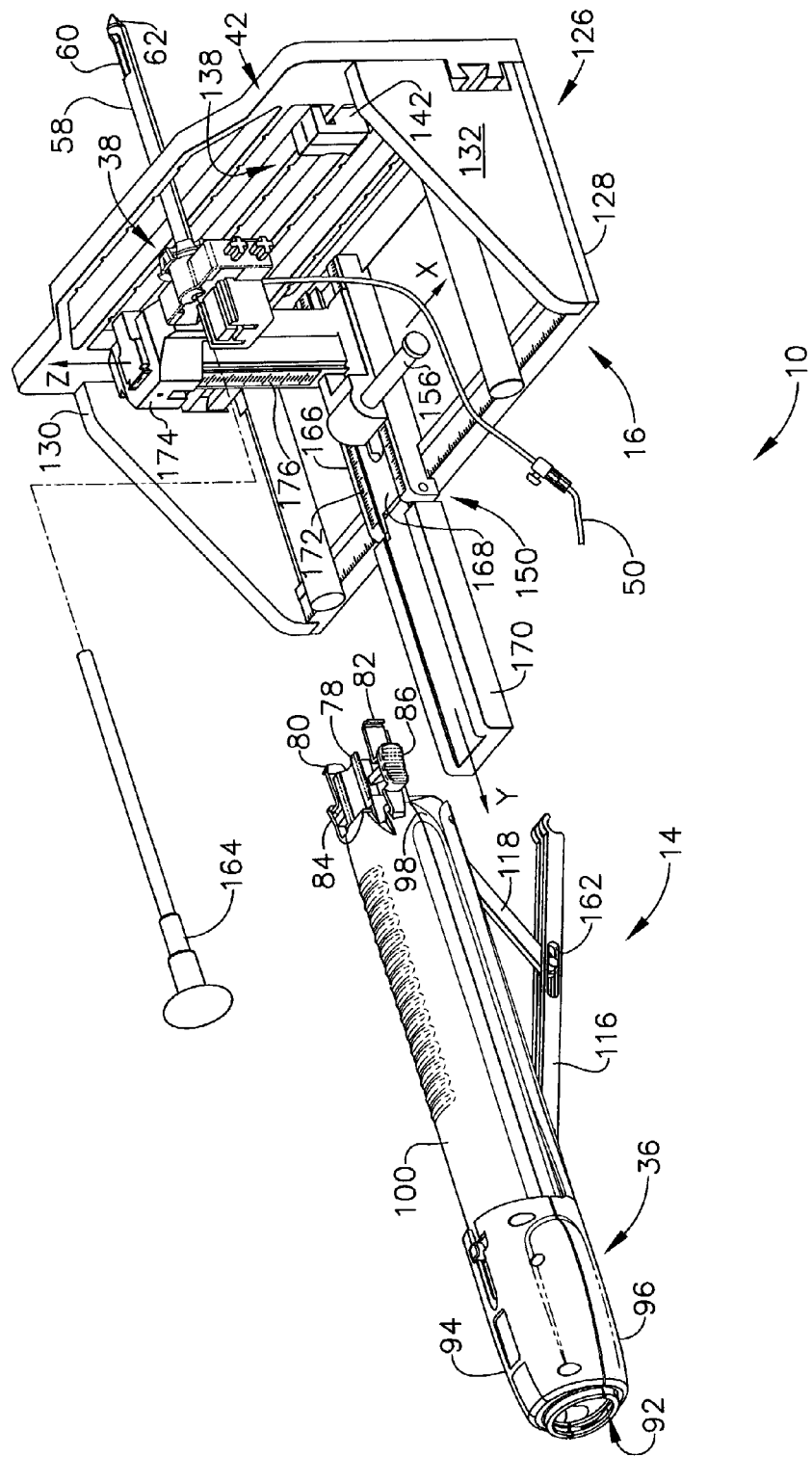
FIG. 11 is an isometric view of the biopsy instrument with the handle portion disconnected from a tower/bracket localization fixture and probe assembly.
Figure 12:
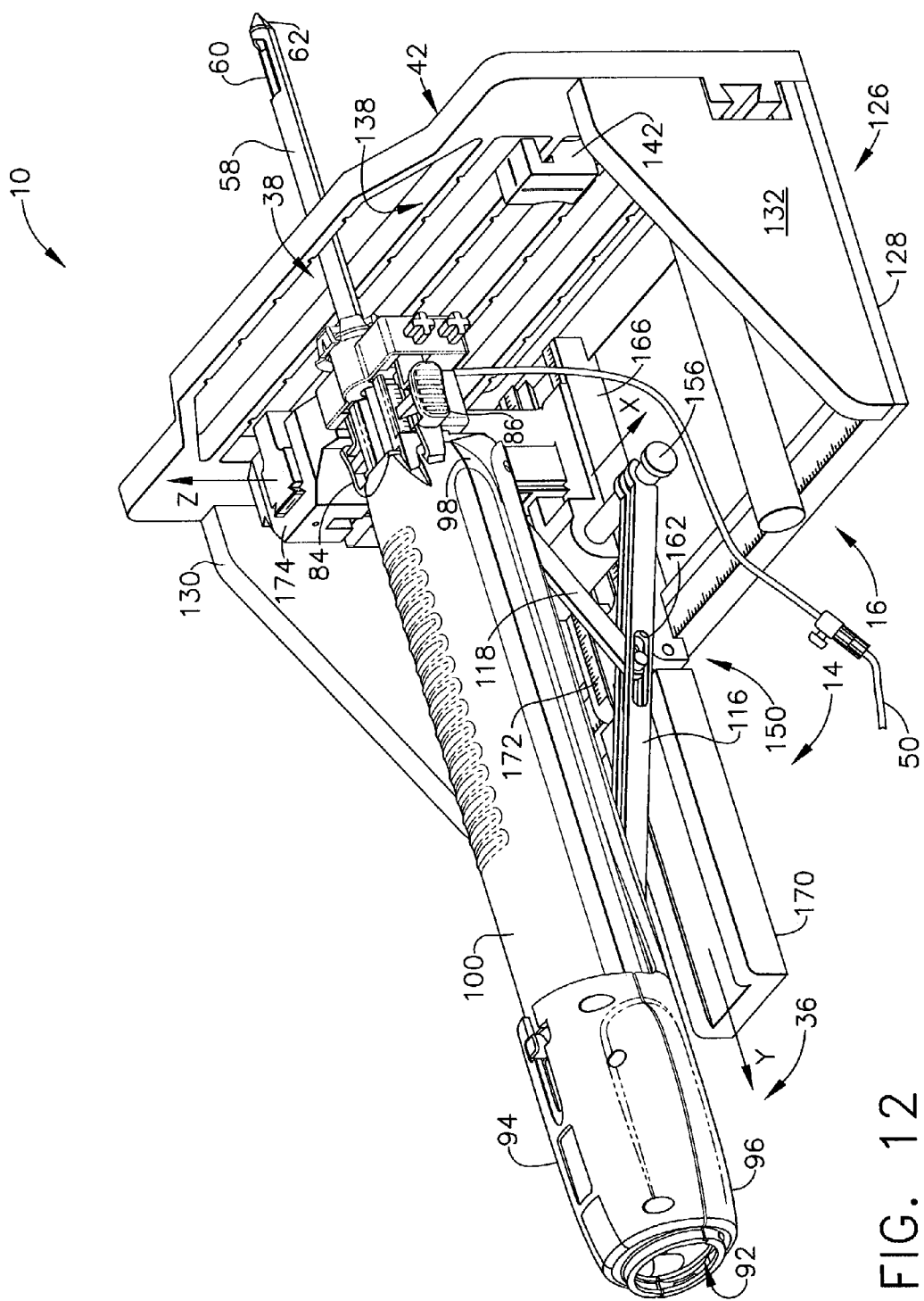
FIG. 12 is an isometric view of the biopsy instrument mounted to the tower/bracket localization fixture of FIG. 11.
Figure 13:
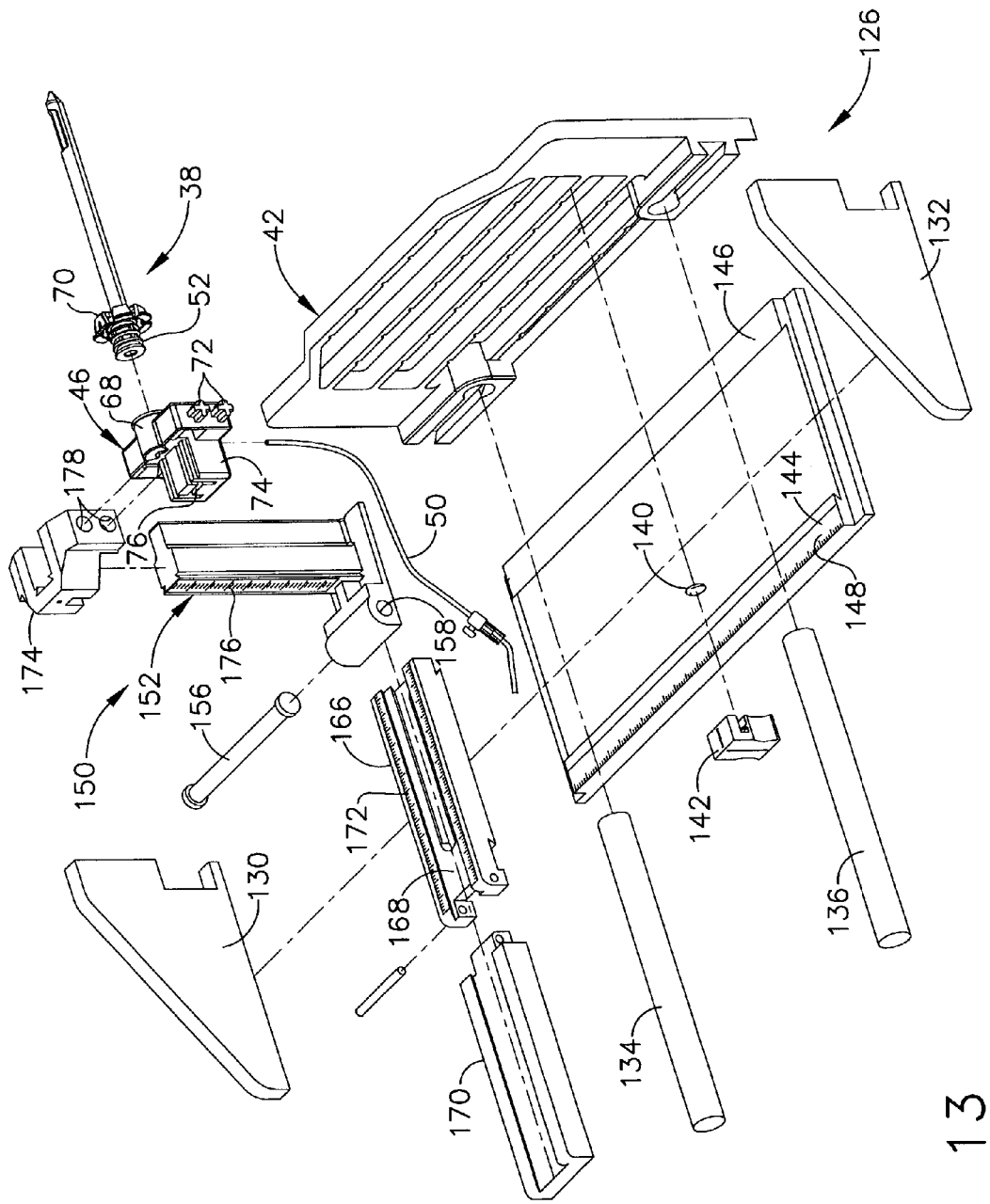
FIG. 13 is an exploded isometric view of the tower/bracket localization version of the localization fixture and probe assembly of the biopsy instrument.
Figure 14:
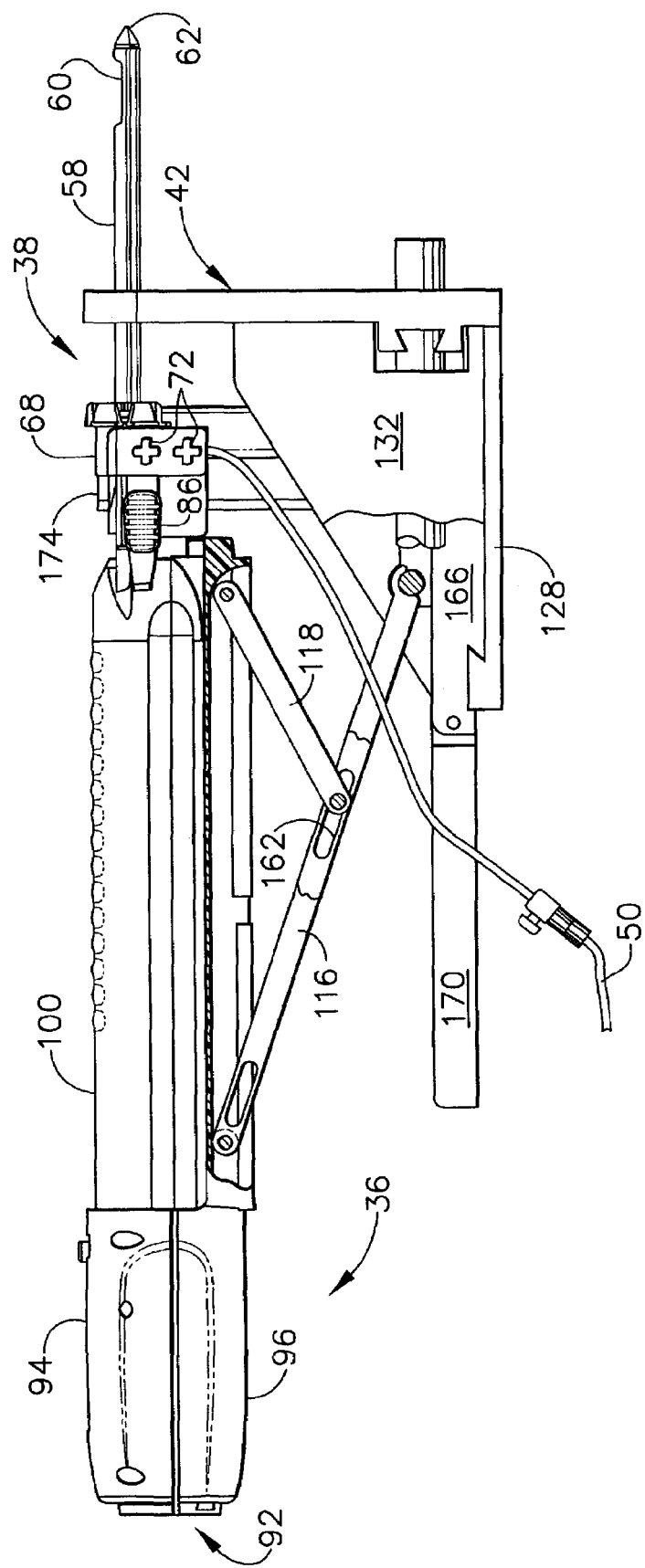
FIG. 14 is a side elevation view of the biopsy instrument in partial section to illustrate a tower/bracket support for stabilizing the handle and probe assembly of the biopsy instrument.

With the handle 36 detached from the probe assembly 38 as depicted in FIG. 11, an obturator stylet 164 is slid into the cutter lumen 56 to close the cutter port 88. The stylet 164 may have radially-oriented through holes near its distal end to maintain fluid communication between the vacuum lumen chamber 64 and cutter lumen 56. Alternatively, the stylet 164 may be partially withdrawn, allowing the cutter port 88 to be in fluid communication with the conduit 50

A slide 166 includes a grooved underside to horizontally slide on rails 144, 146 of the slide plate 128. The slide 166 also includes a central channel 168 oriented in the Y-axis depth dimension to guide the pedestal 152 as it slides in the Y-axis direction. Sufficient range of motion in depth is achieved with a pivoting depth slide 170, aligned and pivotally attached to the slide 166. With the pivoting depth slide 170 in its lowest, horizontal position, the pedestal 152 may be slid outward sufficiently for the probe assembly 38 to be out of the compression plate 42. With the pedestal 152 distally slid onto the slide 166, the pivoting depth slide 170 may be pivoted upward or otherwise removed. Depth indicia 172 along the central channel 168 give the surgeon an indication of the insertion depth of the probe assembly 38.

A vertical slide 174 slides on the pedestal 152 for vertical positioning along the Z-axis, with a measurement provided by vertical indicia 176 on the pedestal 152. Holes 178 on each lateral side of the vertical slide 174 allow mounting of the probe housing 46 on either side by insertion of attachment probes 72.

Figure 15:
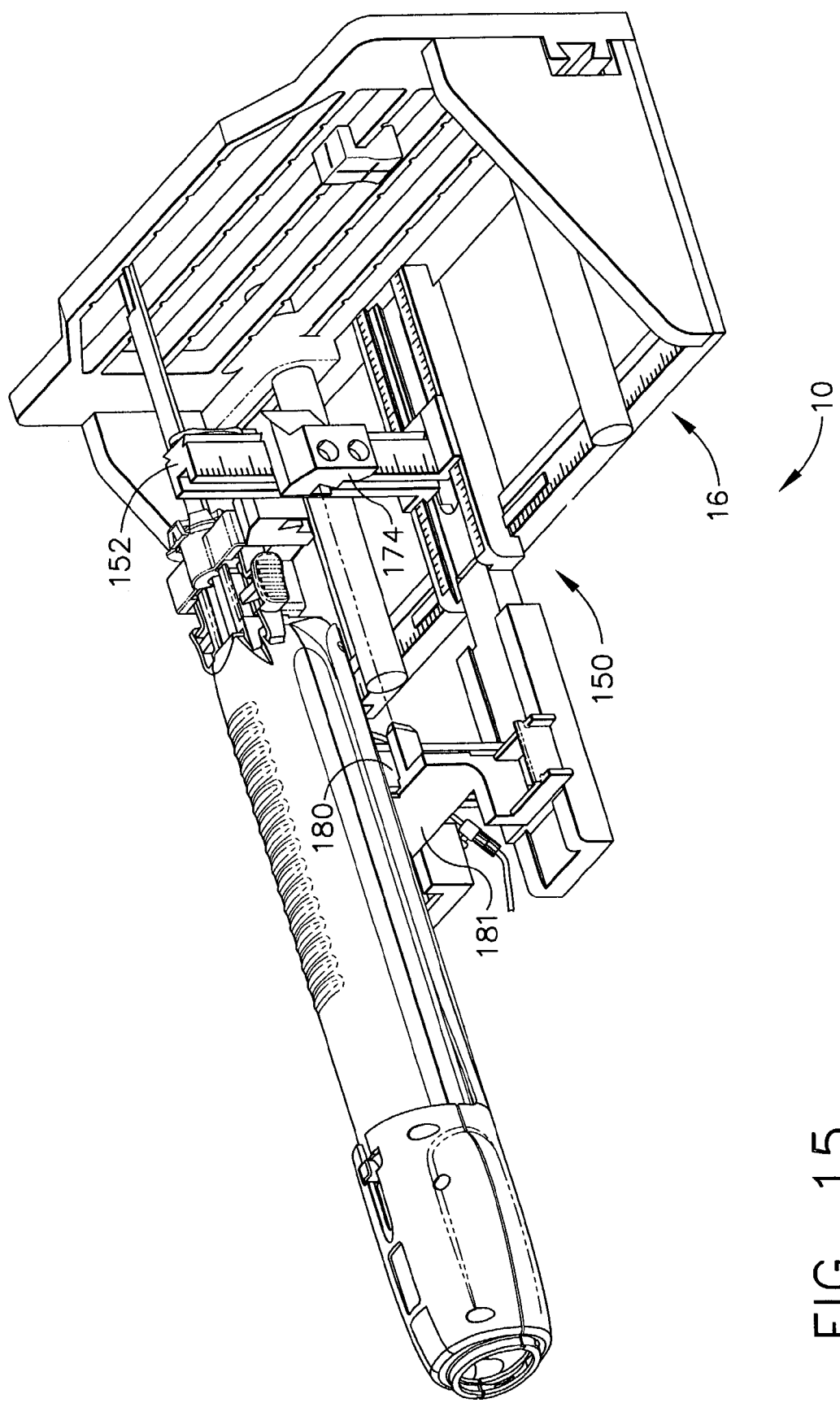
FIG. 15 is a side elevation view of the dual tower support version of the localization fixture positioning a detachable probe assembly with its dual lumens closed by a vacuum conduit and an obturator stylet.
Figure 16:
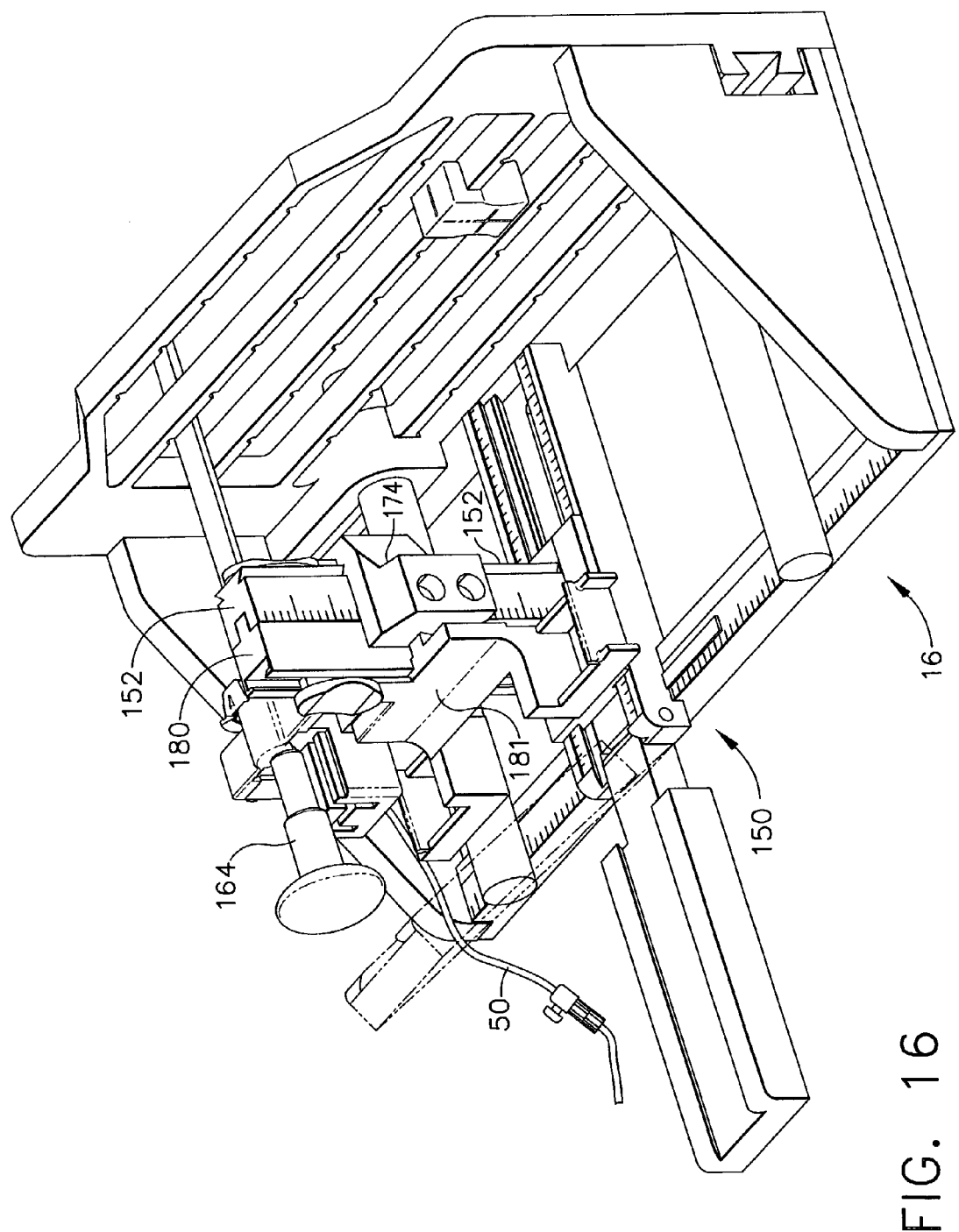
FIG. 16 is an isometric view of the biopsy instrument mounted to a dual tower localization fixture.

FIGS. 15-16 depict a second version of the mounting device 150 that uses a second vertical pedestal 180 in lieu of a brace assembly to support the handle 36. The probe housing 46 is also depicted as attached to the opposite side of the first vertical pedestal 152. A second vertical slide 181 of the second vertical slide 180 advantages contacts the first vertical slide 174, as shown in FIG. 16, so that setting the vertical height for both is accomplished in one step. Each vertical slide 174, 181 moves in a ratchet fashion against its respective vertical pedestal 152, 180, and thus remains in position after being separated from one another as shown in FIG. 15. Moreover, the close nesting of the two vertical pedestals 174, 180 enhances the ability to minimize the proximal displacement of the localization fixture 16 when used within the close confines of a closed MRI magnetic bore 24. It will be further appreciated that the second vertical slide 181 includes a shaped area that engages the underside of the handle 36 in such a way as to correctly align the handle 36 at the same X-axis horizontal dimension as the probe assembly 38.

Figure 17:
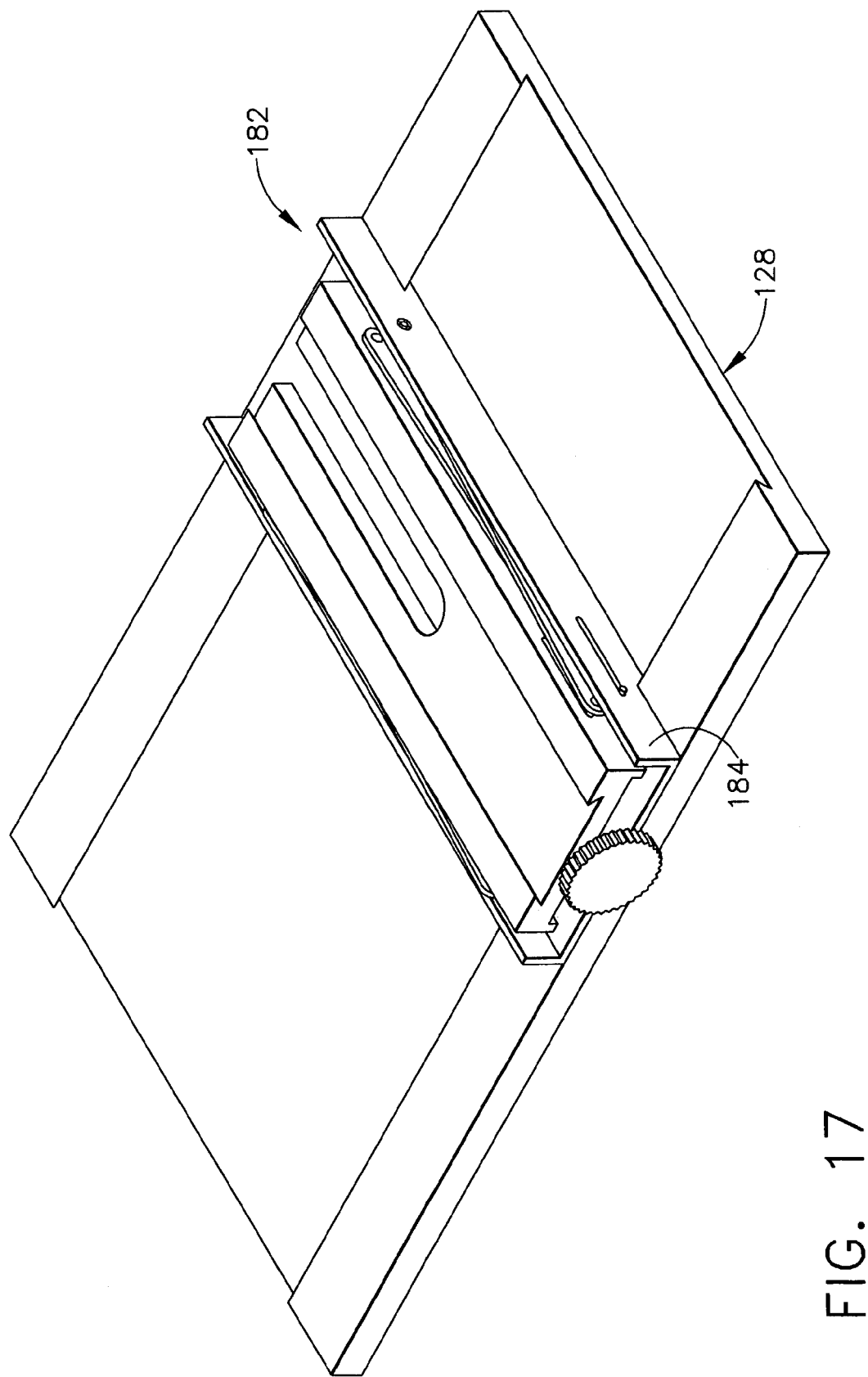
FIG. 17 is an isometric view of the slide plate of a localization fixture guiding a scissors support in a lowered position for vertically orienting a biopsy instrument.
Figure 18:
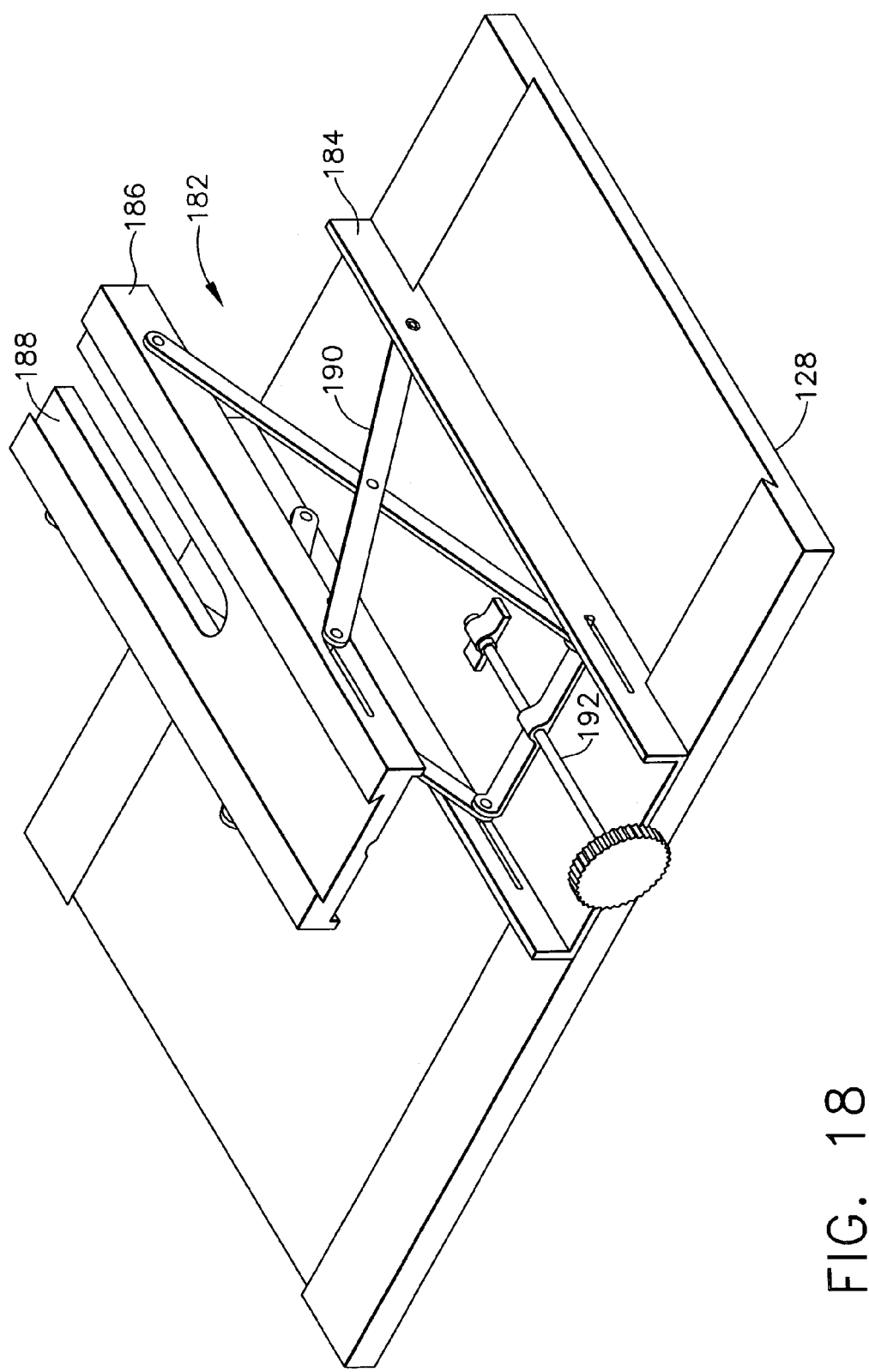
FIG. 18 is an isometric view of the slide plate of a localization fixture guiding the scissors support in a raised position for vertically orienting a biopsy instrument.

FIGS. 17-18 depict a third version of the mounting device 150 wherein the slide 166 and pedestal 152 are replaced with a scissors table assembly 182 that includes a first slide 184 for horizontal movement on the slide plate 128. A depth slide 186 is nested within a top channel 188 of the first slide 182. With particular reference to FIG. 18, a pair of scissors braces 190 are extended when drawn together with a screw 192, thereby elevating the depth slide 186 with respect to the first slide 184. It will be appreciated that the third version of the mounting device 150 advantageously provides a level support for both the detachable probe assembly 38 as well as the biopsy handle 36 without having to perform two vertical adjustments, as well as not having to perform two separate attachments for each of the handle 36 and probe assembly 38.

Figure 19:
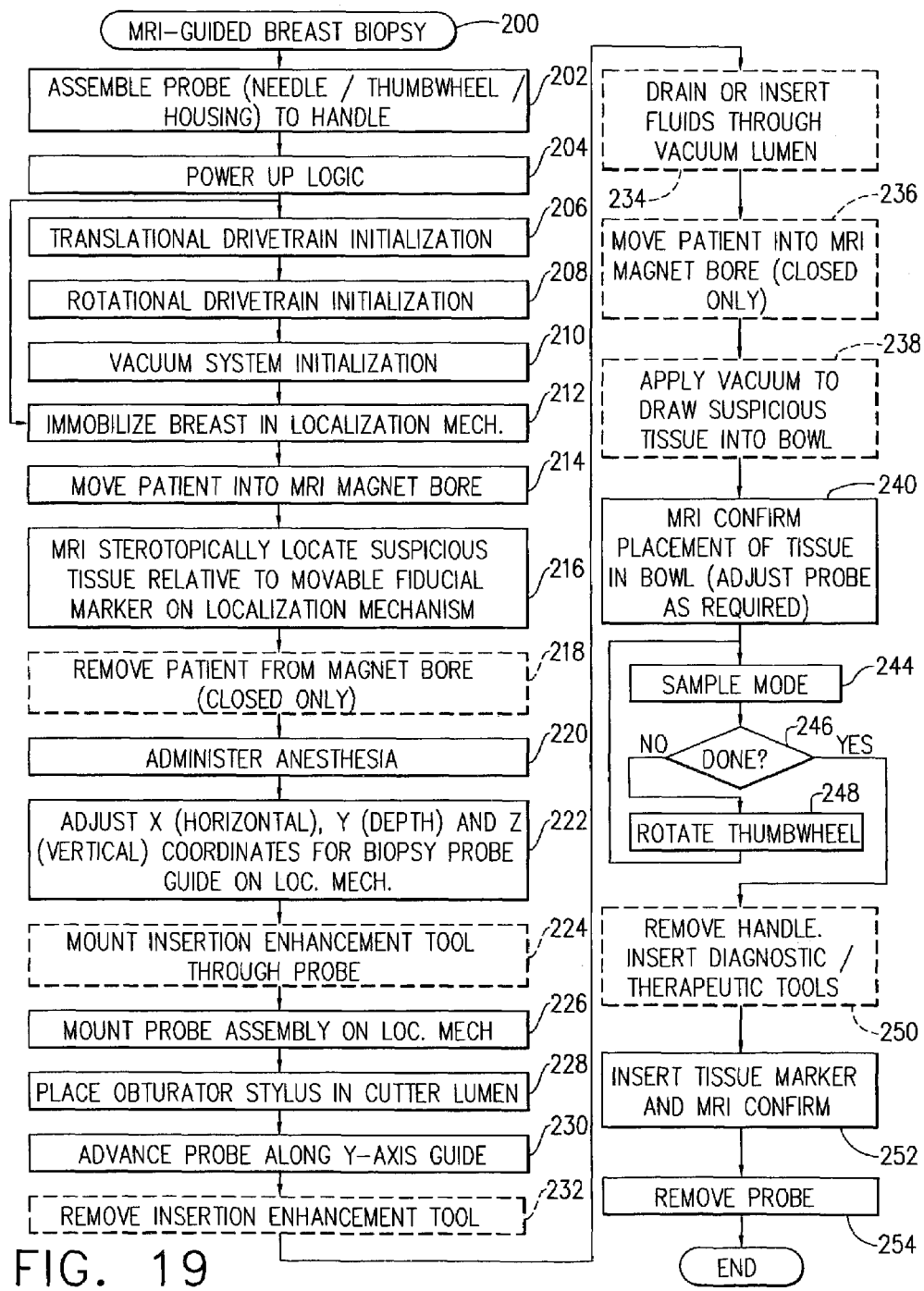
FIG. 19 is a sequence of clinical operations for using the detachable MRI-guided biopsy instrument of FIG. 1 in both open and closed MRI machines.

FIG. 19 depicts a sequence of operations, or method 200, for performing an MRI-guided breast core biopsy that accurately and quickly performs a core biopsy even in a closed MRI. Moreover, the method takes full advantage of the stereotopic location information rendered from the MRI scan to position an MRI compatible core biopsy probe without the necessity of continuous imaging of the distal tip of the biopsy probe.

Prior to performing a clinical breast biopsy, the equipment is initialized to ensure proper function. Thus, in block 202, the probe that comprises a needle, thumb wheel and housing is assembled with the handle. The assembled biopsy tool is connected via a power cord to a control module and the system is powered up, initiating power up logic in the control module (block 204). Parameters for rotation speed and translation distances are loaded. If the control module determines that the system has not been powered up recently, such as 60 minutes, then initialization logic is performed. Thus, translational drivetrain initialization is performed (block 206); rotational drivetrain initialization is performed (block 208); and vacuum system initialization is performed (block 210). If initialization is not required, then blocks 206-210 are bypassed.

Then, the patient's breast is immobilized in the localization mechanism (block 212) and the patient is moved into the MRI magnet bore (block 214). An MRI scan is performed to stereotopically locate suspicious tissue with reference to a movable fiduciary marker on the localization mechanism (block 216). For a closed MRI magnet bore, the patient is then removed (block 218), which is not necessary for an open bore. Anesthesia is administered prior to the minimally invasive vacuum assisted core biopsy procedure (block 220). Using the X-Y-Z positioning capabilities of the localization mechanism, the positioning guides on the localization mechanism are positioned for insertion to the predetermined biopsy site (block 222).

Optionally, insertion may be enhanced by use of an insertion tool installed through the probe assembly 38 (block 224). For instance, an ultrasonic cutting tip, extender, and outer tube assembly may be inserted through the probe assembly 38 through a slot in the needle tip 62, or exiting from the sample port 60 to be snapped onto the needle tip 62. This could be accomplished with a housing on the ultrasonic device that is configured to snap onto the needle 58, similarly to how a trocar obturator snaps onto the trocar cannula. Then, the ultrasonic tip is energized prior to insertion into the patient.

The probe assembly is mounted on the localization mechanism (block 226) at the designated X-Z coordinate and with the mounting device withdrawn along the depth axis. The cutter lumen is sealed with an obturator stylet (block 228), if not otherwise sealed by a tool in block 224. The vacuum lumen may be similarly sealed (e.g., stopcock attached to vacuum lumen access conduit 50) or be used to aspirate fluid and tissue during insertion. Then the probe is advanced along the Y-axis, guided by the localization mechanism to avoid misalignment (block 230). Once in place, if an insertion enhancement tool was installed in block 224, then this tool is withdrawn through the cutter lumen of the probe assembly (block 232).

With the probe in place, various fluid transfers may advantageously take place through the probe assembly (block 234). For example, vacuum may be applied through the vacuum lumen with the sample port exposed to drain any hematoma or air bubble formed at the biopsy site. Treatment fluids may be inserted directly to the biopsy site, such as anesthesia or MRI contrast agent. If the patient is to be scanned in a closed magnet bore, then the patient is moved back into the bore for scanning (block 236). In addition, vacuum may optionally be applied to the biopsy site to draw in suspicious tissue into the bowl of the sample port for confirmation prior to cutting the sample (block 238). Then, the MRI scan is performed to confirm placement of tissue in the bowl of the probe assembly, and adjustment of the probe assembly placement and re-scans are performed as required (block 240).

Sample mode is selected through the control module to perform the sequence of steps to translate and rotate the cutter according to predetermined settings, with vacuum assist to draw in the sample and to retract the sample along with the cutter to the sample window (block 244). If more samples at this biopsy site are required for diagnostic or for treatment purposes (block 246), then the thumb wheel is rotated to reorient the sample port to another angle (block 248), and sample mode is performed again by returning to block 244.

After the core biopsy is performed, the probe assembly provides an excellent opportunity for other minimally invasive diagnostic procedures and treatments without the necessity for another insertion. If the biopsy handle is installed, such as in an open MRI magnet bore, the handle is removed so that the detachable probe assembly may be accessed (block 250). Examples of tools that may be inserted through the probe assembly include: (1) gamma detectors; (2) energized tunneling tips to reduce tunneling forces; (3) inserts to aid in reconstruction of removed tissue (e.g., one or two sided shaver inserts); (4) spectroscopy imaging devices; (5) general tissue characterization sensors {e.g., (a) mammography; (b) ultrasound, sonography, contrast agents, power Doppler; (c) PET and FDG ([Flourine-18]-2-deoxy-2-fluoro-glucose); (d) MRI or NMR, breast coil; (e) mechanical impedance or elastic modulus; (f) electrical impedance; (g) optical spectroscopy, raman spectroscopy, phase, polarization, wavelength/ frequency, reflectance; (h) laser-induced fluorescence or auto-fluorescence; (i) radiation emission/detection, radioactive seed implantation;(j) flow cytometry; (k) genomics, PCR (polymerase chain reaction) -brcal, brca2; (l) proteomics, protein pathway}; (6) tissue marker sensing device; (7) inserts or devices for MRI enhancement; (8) biochips on-a-stick; (9) endoscope; (10) diagnostic pharmaceutical agents delivery devices; (11) therapeutic anti-cancer pharmaceutical agents delivery devices; (12) radiation therapy delivery devices, radiation seeds; (13) anti-seeding agents for therapeutic biopsies to block the release of growth factors and/or cytokines (e.g., chlorpheniramine (CPA) is a protein that has been found to reduce proliferation of seeded cancer sells by 75% in cell cultures.); (14) fluorescent tagged antibodies, and a couple fiber optics to stimulate fluorescence from a laser source and to detect fluorescence signals for detecting remaining cancer cells; (15) positive pressure source to supply fluid to the cavity to aid with ultrasound visualization or to inflate the cavity to under the shape or to reduce bleeding; (16) biological tagging delivery devices (e.g., (a) functional imaging of cellular proliferation, neovacularity, mitochondrial density, glucose metabolism; (b) immunohistochemistry of estrogen receptor, her2neu; (c) genomics, PCR (polymerase chain reaction)-brcal, brca2; (d) proteomics, protein pathway); and (17) marking clips.

Then, a tissue marker is inserted through the probe assembly so that subsequent ultrasonic, X-ray, or MRI scans will identify the location of the previous biopsy (block 252) and the probe is removed (block 254).

Figure 20:
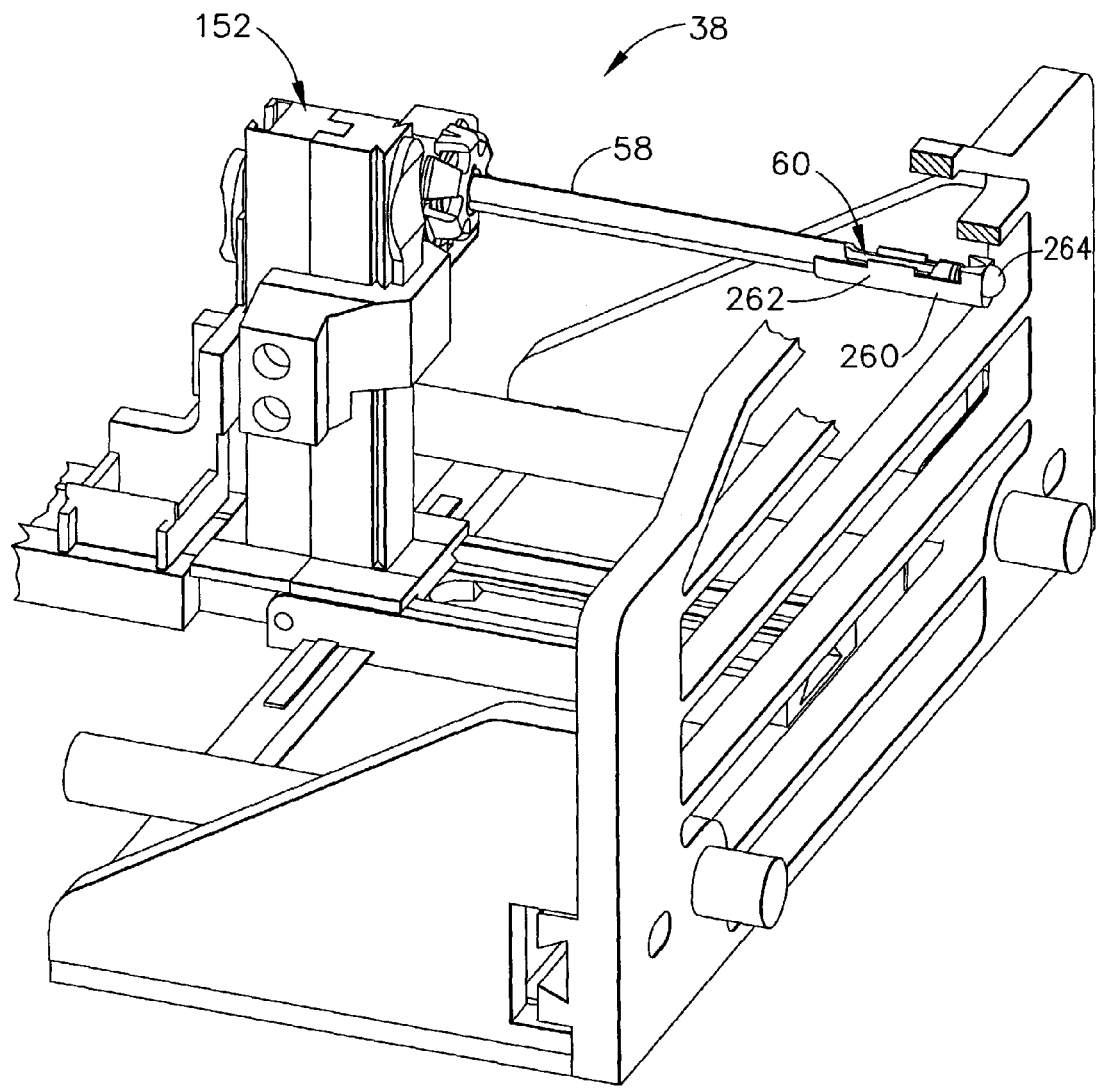
FIG. 20 is an isometric view of a tip protector mounted onto a needle tip of the detachable probe assembly of FIG. 11.
Figure 21:
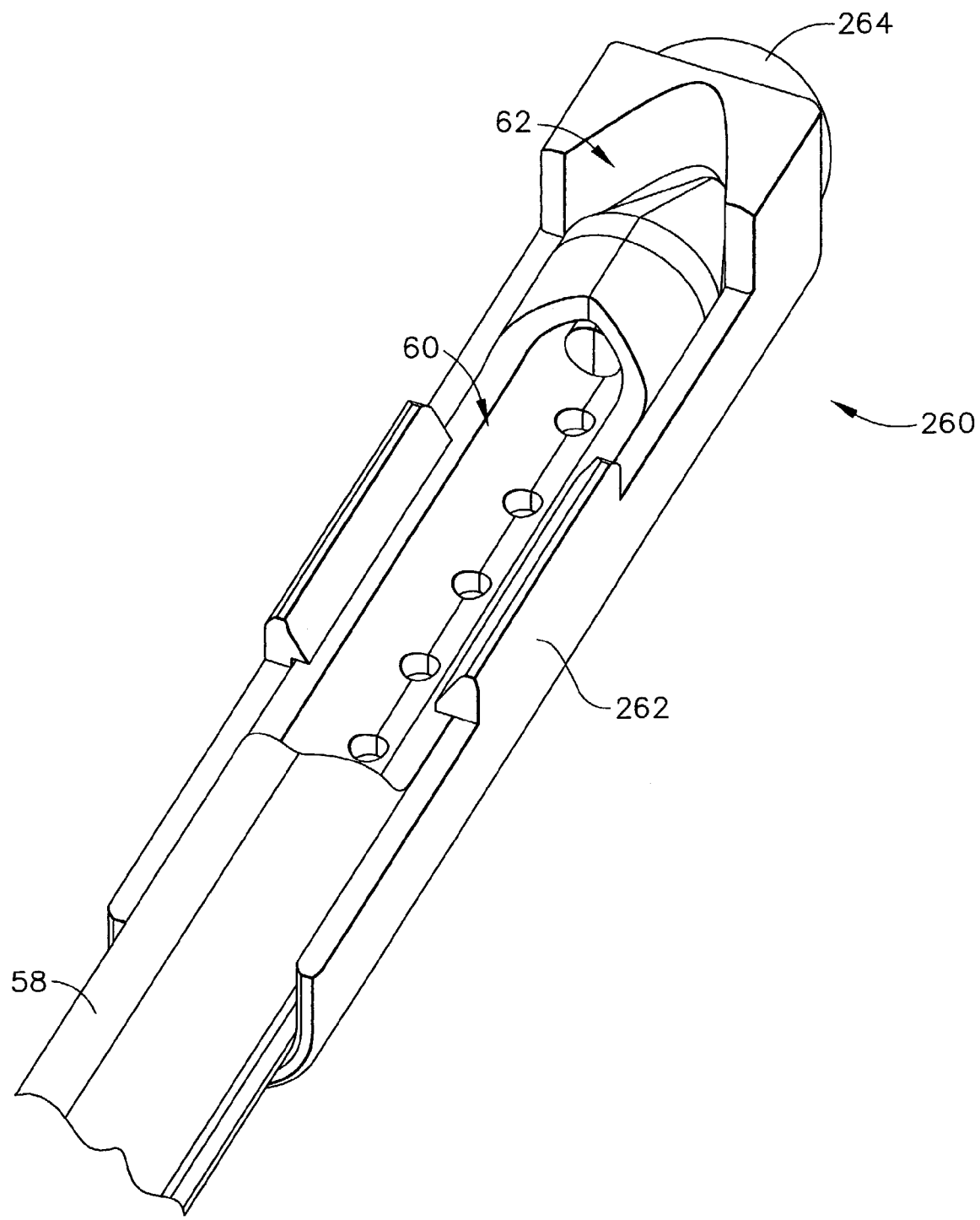
FIG. 21 is an isometric detail view of the trip protector of FIG. 20.

FIGS. 20-21 depict a tip protector 260 that advantageously protects the needle tip 62 of the probe assembly 38 prior to insertion into tissue and simplifies localization of the probe assembly 38 in some instances. Furthermore, the tip protector 260 does not interfere with pre-clinical setup procedures (e.g., testing for vacuum leaks). In particular, the tip protector 260 includes an attachment member 262 with clips onto the needle 58 without obstructing the sample port 60. A distal portion of the tip protector completely encompasses the needle tip 62 with a protection member, depicted as a hemispheric disk 264, that may be placed in contact with a patient's breast without discomfort. In addition, in some applications the hemispheric disk 264 may be comprised of or include an MRI artifact producing material, such as those described above. Since the hemispheric disk 264 is MRI scanned outside of the patient's breast, a stronger artifact may be presented to aid in quickly locating the artifact without obscuring the suspected lesion.

With a fiducial marker integrated into the tip protector 260, there is potentially one less step in the localization process for operators that prefer to position fiducial marker at the closest insertion point to a suspected lesion prior to insertion. Procedurally, with the tip protector 260 in place, the operator would attach the probe assembly 38 onto the pedestal 152 and move the probe assembly 38 up against the breast tissue in the vicinity of where they believe the suspicious tissue to be, based on an earlier diagnostic image. Next, when the distance from this fiducial marker to the lesion is calculated, the "delta" distances are based on where the probe is currently positioned. There is a fixed offset along the Y axis to account for the distance from the fiducial to the middle of the bowl. The attachment member 262 accurately locates the hemispheric disk 264 so that this Y-axis offset is predictable. This would be more intuitive because the delta positions are from where the probe is currently located.

Figure 22:
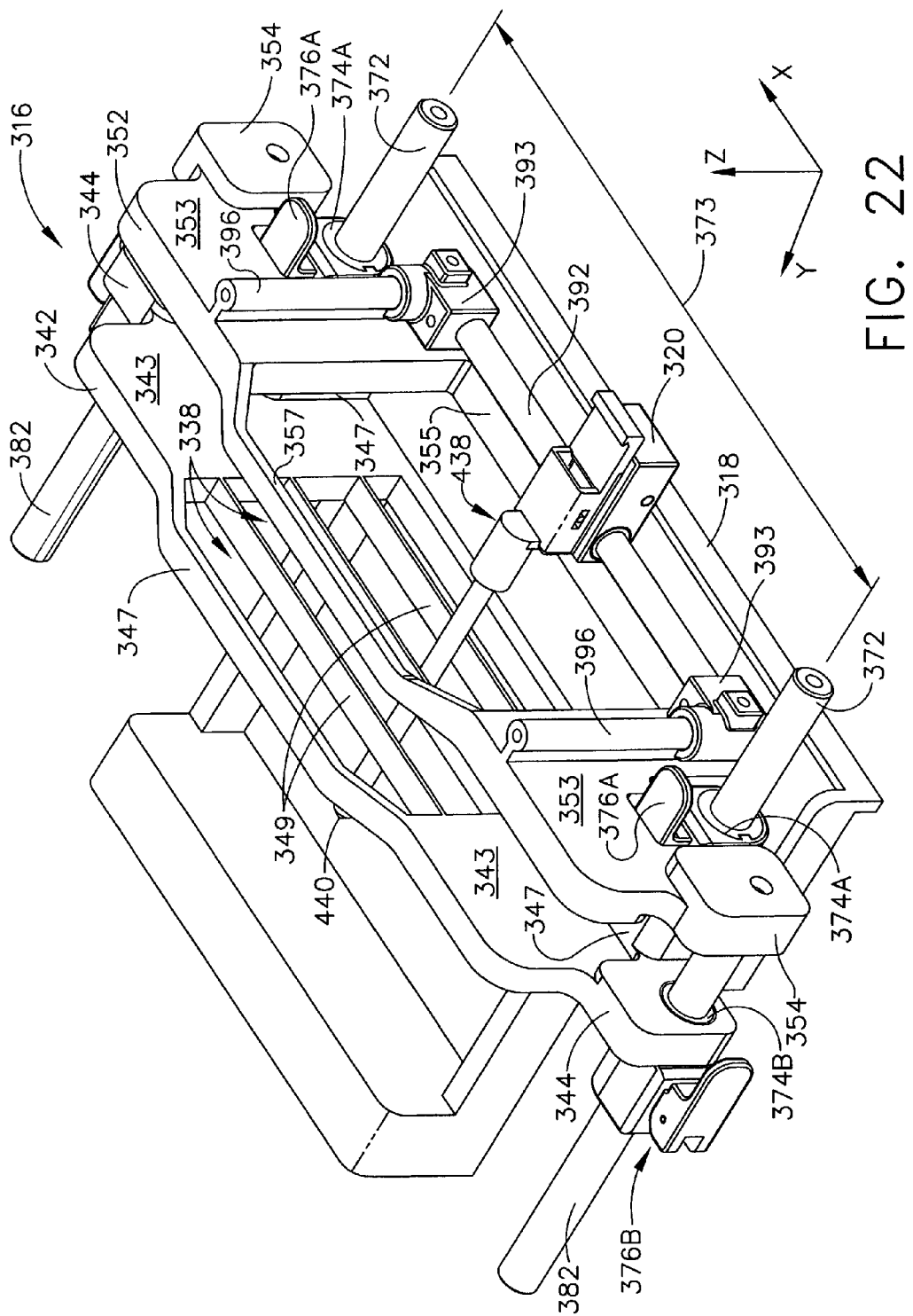
FIG. 22 is an isometric view of one embodiment of a localization mechanism according to the present invention.

FIG. 22 provides an isometric schematic illustration of an embodiment of a fixture mechanism 316 according to the present invention. The fixture mechanism 316 can include a base 318, a movable breast compression plate 342 having apertures for accommodating a biopsy needle (apertures in the form of parallelel slots 338 in FIG. 22), and a probe support plate 352. The probe support plate 352 can be supported to move independently of the breast compression plate 342 in the Y direction. A biopsy probe assembly 438 (including needle with distal tip 440) can be supported on probe support plate 352 to move relative to the probe support plate 352 in the X and Z directions, as described in more detail below. The biopsy probe assembly 438 can be releasably attached to a probe assembly mount 320, such as by a spring loaded mechanism (e.g. ball detent) or other biasing mechanism for reducing clearances between the assembly 438 and the mount 320 (in order to improve positional accuracy of the probe). Probe assembly mount 320 in turn can be supported on support plate 352 to permit movement of mount 320 with respect to support plate 352, as described more fully below.

Still referring to FIG. 22, probe support plate 352 can include plate side portions 353 which are laterally spaced apart in the X direction. A bottom plate portion 355 and a top bridge 357 extend between the side portions 353 and together with the side portions 353 define an opening in the support plate 352 through which a portion of the probe assembly 438 can extend.

Compression plate 342 is supported on slide shafts 372 (which can be rigidly attached to or otherwise fixed relative to the base 318) to translate relative to the base 318 in the Y direction. The Compression plate 342 can be supported by bushings 374A (or other suitable bearings) for permitting sliding of the plate 342 on shafts 372. The bushings can be disposed in bosses 347 which extend from side portions 343. Bushings 374A can extend along shafts 372 to also be disposed within a locking mechanism associated with shaft 372, such as releasable clamp locking mechanisms discussed below. Shafts 372 can include splines, a non circular cross-section or have other anti-rotation features to prevent rotation of the shaft with respect to the plate 342 and for carrying torsional loads.

A locking mechanism 376A can be associated with each support shaft 372 to releasably fix the position of the compression plate 342 in a desired Y location along the shafts 372. A suitable locking mechanism is a toggle clamp manufactured by DE-STAC-CO Industries of Madison Heights, Mich. Other suitable locking mechanisms for releasably fixing the plate 342 at a desired location along the shafts 372 include, without limitation, friction locks, set screws, over center clamps, and spring loaded clamps. In one embodiment, a locking clamp can include a three position lever, wherein in an upright position the lever unlocks the clamp, in a horizontal position the lever locks the clamp, and wherein the lever can be depressed against a biasing spring to a third position to unlock the clamp while the lever remains depressed.

The movable breast compression plate 342 can include plate side portions 343 which are laterally spaced apart in the X direction. The plate 342 can include a bridge 347 and ribs 349 which extend laterally between the side portions 343 to provide apertures (slots 338 in FIG. 22) for permitting passage of the biopsy needle in the Y direction. Alternatively, the apertures can be provided in the form of an array or grid of openings, and the apertures can be formed in a separate insert that is attached to plate 342.

The movable breast compression plate 342 engages two shafts 382 at bushings 374B. Bushings 374B are shown disposed in bosses 344. Bosses 344 extend laterally outwardly from each plate side portion 343 of compression plate 342. Breast compression plate 342 can slide in the Y direction relative to shafts 382. Accordingly, breast compression plate 342 is supported to slide relative to both shafts 372 and shafts 382 in the Y direction. Shafts 382 are generally parallel to, or collinear, with shafts 372, and shafts 382 have ends which can be fixed to probe support plate 352. In the embodiment in FIG. 22, shafts 382 are cantileverd from bosses 354 which extend laterally outwardly from each plate side portion 353 of the support plate 352. Sliding movement of shafts 382 with respect to plate 342 results in motion of plate 352 with respect to plate 342 in the Y direction. A locking mechanisms 376B can be associated with each shaft 382 to releasably fix breast compression plate 342 with respect shaft 382 (and also with respect to plate 352) in the Y direction. Shafts 382 can have splines, non circular cross sections, or otherwise incorporate anti rotation features for carrying torsional loads.

The center to center spacing of shafts 372, labeled 373 in FIG. 22, can be selected to reduce cocking or misalignment of plate 342 and to accommodate the movement of probe assembly 438 in the X direction. In one embodiment, the spacing 373 is at least about 6 inches, more particularly at least about 10 inches, and still more particularly at least about 12 inches. The center to center spacing of shafts 382 can be the same as or different than the spacing of shafts 372, and in FIG. 22 is shown to be greater than the spacing of shafts 372.

Still referring to FIG. 22, the probe assembly 438 is supported on the probe support plate 352 so that the probe assembly can move in the X and the Z direction relative to the plate 352. The probe assembly can be releasably attached to probe mount 320. The probe mount, in turn can be supported by a bushing or other bearing device to permit sliding of the probe mount 320 on a shaft 392 for translation of the probe mount 320 and probe assembly 438 in the X direction. A locking mechanism (not shown)) can be used to releasably fix the mount 320 (and so probe assembly 438) at a desired X direction location along the shaft 392.

Shaft 392 can be supported to be movable in the Z direction relative to plate 352. In FIG. 22, shaft 392 has its opposing ends supported in support blocks 393. Support blocks 393 can include bushings or other bearing devices to provide sliding of the blocks 393 in the Z direction on two generally parallel rails 396. Rails 396 are fixed to support plate 352 (one rail 396 associated with each side portion 353 in FIG. 22), and rails 396 extend along their lengths in the Z direction. Accordingly, blocks 393 (and so shaft 392) can be positioned along rails 396 to position the probe assembly 438 in a desired Z direction location. A locking mechanism (not shown) can be associated with each support block 393 to lock the shaft 392 (and so probe assembly 438) in a desired Z direction location.

Figure 23:
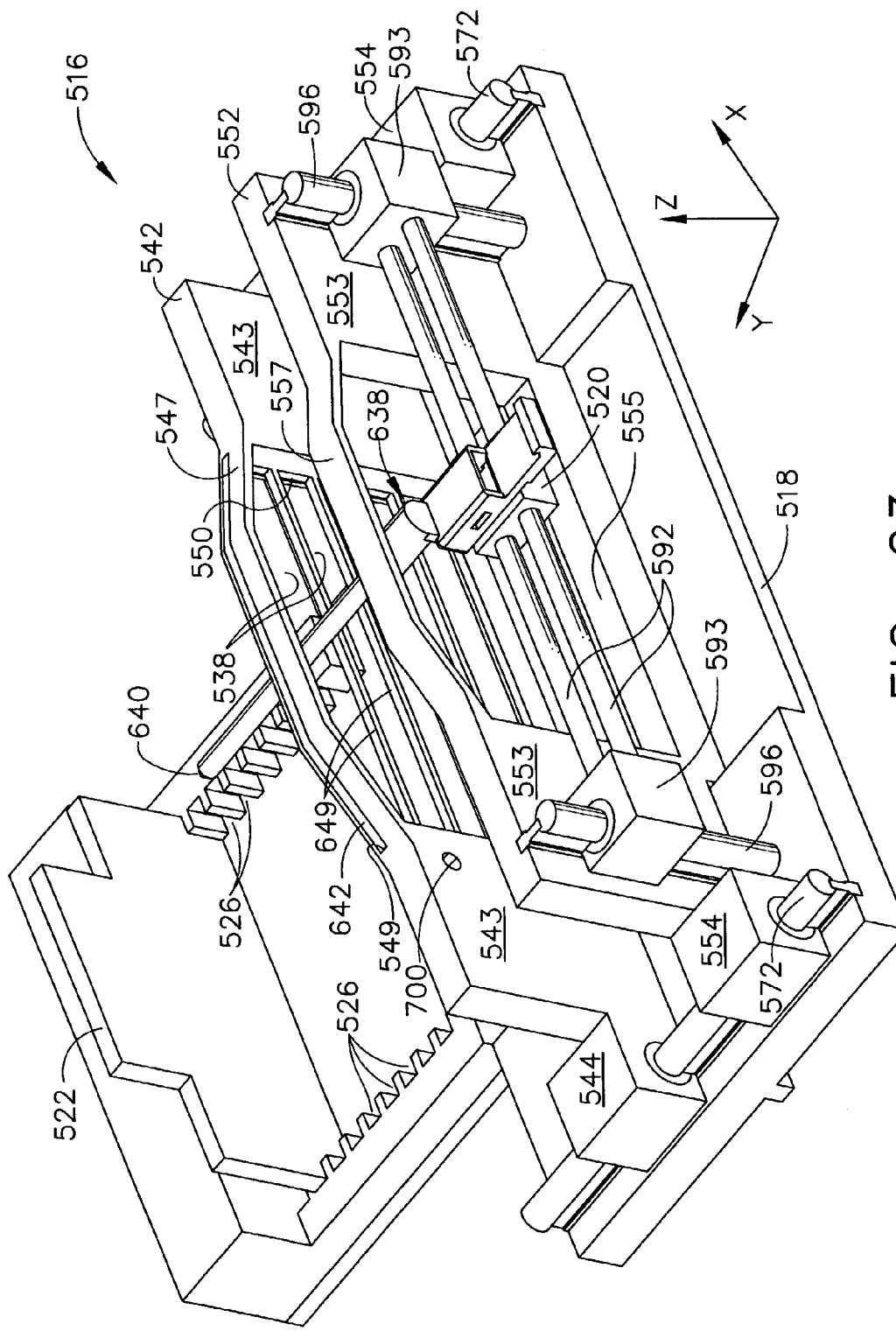
FIG. 23 is an isometric view of an alternative embodiment of a localization mechanism according to the present invention.

FIG. 23 provides an isometric schematic illustration of another alternative embodiment of a fixture mechanism 516 according to the present invention. The fixture mechanism 516 can include a base 518, a movable breast compression plate 542 having parallel slots 538 (through which needle point 640 may pass), and a probe support plate 552 for supporting a probe assembly 638. FIG. 23 also illustrates a medial breast compression plate 522 which is positioned in one of a series of opposing slots 526 formed in the base 518. The Y direction position of the plate 522 relative to the frame can be varied in discrete intervals by positioning the plate 522 in different pairs of opposing slots 526.

The probe support plate 552 in FIG. 23 is supported on two generally parallel slide support rails 572. Support plate 552 is slidable on rails 572 relative to the base 518 in the Y direction. Support rails 572 can be joined to base 518 along substantially their entire length, as shown in FIG. 23, to minimize cantilever loads and resulting positioning error. In FIG. 23, breast compression plate 542 is supported on the same slide rails 572, and each of the plates 542 and 552 can be positioned along the rails 572 at desired Y direction locations along the rails. Locking mechanisms (not shown) can be used to releasably fix the plates 542 and 552 in desired Y direction positions along the rails 572. A biopsy probe assembly 638 (including needle with distal tip 640) is supported on the probe support plate 552 to move relative to the plate 552 in the X and Z directions, as described more fully below.

Still referring to FIG. 23, probe support plate 552 can include plate side portions 553 which are laterally spaced apart in the X direction. A bottom plate portion 555 and a top bridge 557 extend between the side portions 553 and together with the side portions 553 define an opening in the support plate 552 through which a portion of the probe assembly 638 can extend. Bosses 554 on each plate portion 553 can include bushings or other suitable bearing devices for sliding support of plate 552 on rails 572.

The movable breast compression plate 542 can include plate side portions 543 which are laterally spaced apart in the X direction. The plate 542 can include a bridge 547 and ribs which extend laterally between the side portions 543 to provide slots 538. Alternatively, the slots can be provided by a separate insert that is attached to plate 542. In FIG. 23, an insert 642 is shown which includes ribs 649. The insert 642 can slide into a slot 549 formed through bridge 547, and the insert 642 can engage opposing side slots 550 in the plate side portions 543. Plates 542 can include bosses 544 extending laterally outwardly from side portions 543. Bosses 544 can include bushings for supporting the plate 542 for sliding on rails 572.

Rails 572 can have splines, non circular cross sections, or otherwise incorporate anti rotation features. The center to center spacing of rails 572 can be selected to prevent cocking of plate 542 and 552 on rails. In one embodiment, the spacing is at least about 6 inches, more particularly at least about 10 inches, and still more particularly at least about 12 inches.

Still referring to FIG. 23, the probe assembly 638 can be releasably attached to a probe mount 520, such as by a spring loaded mechanism. Probe mount 520 is supported on the probe support plate 552 so that the probe mount and probe assembly can move in the X and the Z direction relative to the plate 552. The probe mount 520 can be supported by a bearing on one or more shafts 592 (two shafts shown in FIG. 23) for translation in the X direction. A locking mechanism (not shown) can be used to releasably fix the probe mount 520 at a desired X direction location along the shafts 592.

The shafts 592 can be supported to be movable in the Z direction relative to plate 552. In FIG. 23, shafts 592 have opposing ends supported in support blocks 593. Support blocks 593 can include bushings or other suitable bearing surfaces for sliding generally parallel rails 596. Rails 596 are fixed to support plate 552 (one rail 596 associated with each side portion 553 in FIG. 23), and rails 596 extend along their lengths in the Z direction. Accordingly, shaft 592 can be positioned along rails 596 to position the probe mount 520 and probe assembly 638 in a desired Z direction location. A locking mechanism (not shown) can be associated with each support block 593 to lock the shafts 592 (and so probe assembly 638) in a desired Z direction location.

One or more fiducial markers can be attached to one or both of the plates 542 and 552 to present an artifact which is detectable in a magnetic resonance image. In FIG. 23 a fiducial marker 700 is shown positioned on breast compression plate 542. If desired, position encoders can be associated with each axis of motion, and the output from the encoders can be transmitted to a receiving source, such as a computer control and/or a visual readout display (e.g. an LED display). Position encoding can be accomplished using any suitable encoding means, including without limitation mechanical, optical, laser, or magnetic encoding means. A suitable encoder is an EM1 Optical Incremental encoder Module available from US Digital of Vanouver, Wash., USA. A position encoder can be associated with each of plates 542 and 552 to identify the Y position of the plates' position along rails 572. A position encoder can be associated with one or both of blocks 593 to identify the position of the blocks in the Z direction along rails 596. A position encoder can be associated with the probe mount 520 to identify the position of the mount 520 in the X direction along shafts 592. One portion of the encoder system (such as a linear strip with indicia lines) can be attached or otherwise associated with a shaft or rail (e.g. rails 572), and another portion of the encoder system (such as the sensor read head) can be attached to or otherwise associated with a part moving with respect to the shaft or rail (e.g blocks 593). The position information from the encoders can be used to determine, transmit, and/or visually display the X, Y, and Z position of the probe assembly (including needle tip 640).

In FIG. 23, rails 572 provide a first pair of generally parallel, elongated sliding supports oriented in a first direction (Y), and rails 596 provide a second pair of generally parallel, elongated sliding supports oriented in a second direction (Z) perpendicular to the first direction. Biopsy probe support plate 552 is adapted to support the biopsy probe 638 in a position that is everywhere between the two parallel rail supports 572 (when viewed along the Z axis) and between the two rail parallel supports 596 (when viewed along the Y axis), and with biopsy probe 638 being supported on probe mount 520 for sliding movement along a third direction (X) perpendicular to the first and second directions. Positioning the support rails 572 and 596, one each on each side of probe assembly 638, so that the probe assembly is between each pair of generally parallel supports, can be helpful in minimizing probe misalignment and positioning inaccuracy.

In using the apparatus of FIGS. 23, the patient's breast can be immobilized in the localization mechanism by advancing the lateral compression plate along the Y-axis. With the breast relatively immobilized, the patient is moved into the MRI magnet bore.

An MRI scan of the breast is performed to locate suspicious tissue with reference to a fiduciary marker located on the localization mechanism. For a closed MRI magnet bore, the patient is then removed from the magnet bore (not necessary for an open bore). By scrolling through slice images of the breast, the MRI system allows the clinician to place a cursor on the suspicious tissue defining the coordinates of that point in space. Likewise, the clinician can also select the slice image that contains the fiducial marker and place a second cursor on it defining its coordinates. By comparing the two sets of coordinates, the relative position between the fiducial marker and the suspicious tissue can be calculated. The probe assembly 638 can then be mounted on probe mount 520 on the localization mechanism. Using the X-Y-Z positioning capabilities of the localization mechanism, positioning guides on the localization mechanism are positioned at the fiducial marker and the X-Y-Z positions are zeroed-out to set the reference point. The probe assembly mount 520 is then moved along shafts 592 in the X-axis direction the calculated relative distance and its position along the X-axis is fixed with the locking mechanism. The probe assembly mount 520 is then moved in the Z direction by sliding blocks 593/shafts 592 on rails 596 the calculated relative distance and its position along the Z-axis is fixed. Lastly, the probe assembly needle tip 640 is inserted into the breast by advancing the probe support plate 552 along the Y-axis on rails 572 the calculated relative distance to the predetermined biopsy site and its position is fixed along the Y-axis. The actual biopsy is then performed.

Figure 24:
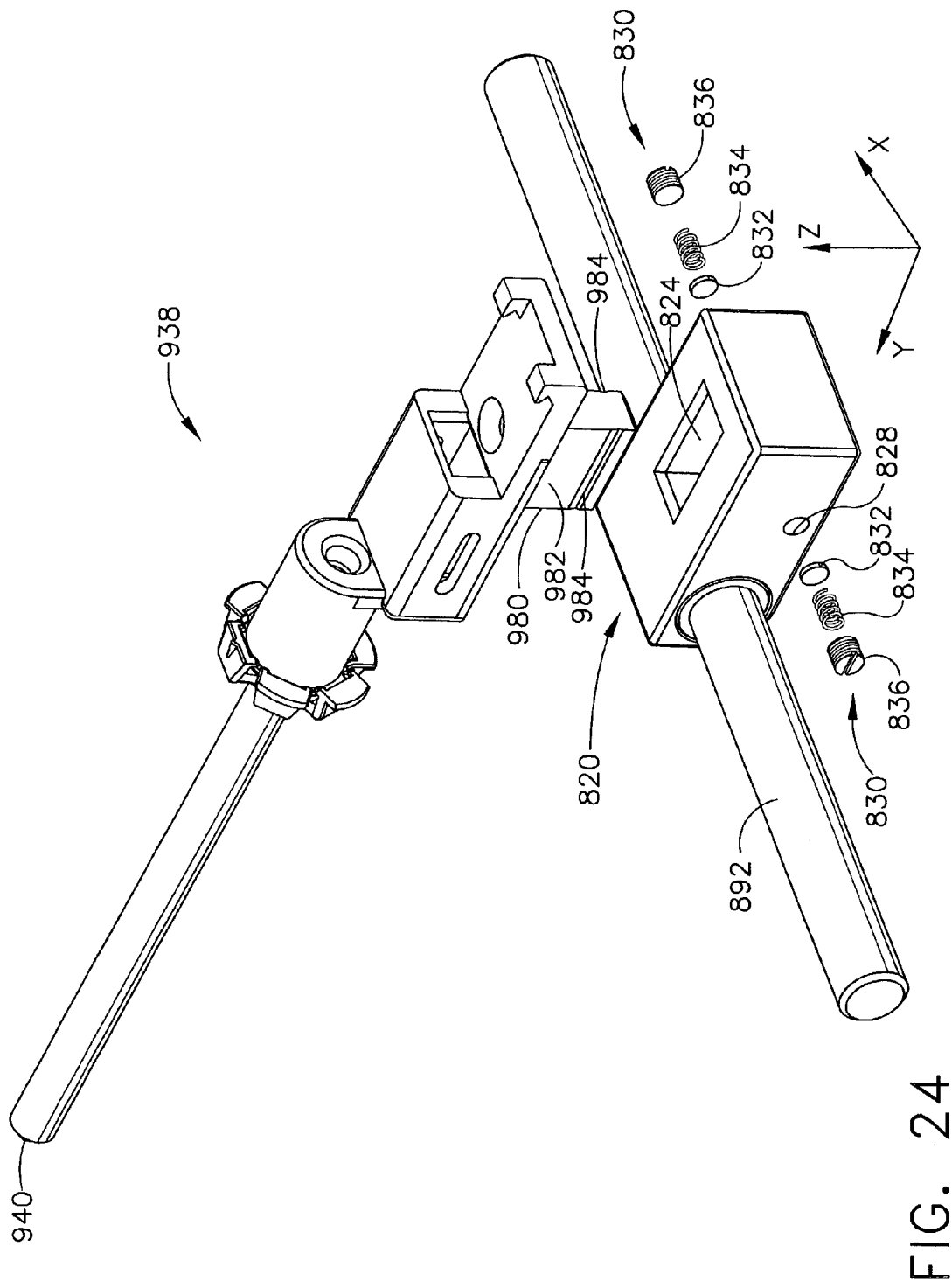
FIG. 24 is an isometric view of a biopsy mount employing a ball detent mechanism for releasably engaging a biopsy probe assembly.

FIG. 24 provides an isometric schematic illustration of a biopsy probe assembly (designated 938) and a probe mount (designated 820) incorporating a spring loaded "ball detent" mechanism for use in releasably attaching the probe assembly to the probe mount. In FIG. 24, probe mount 820 is shown supported for sliding motion in the X direction on a shaft support designated 892. Shaft 892 can include splines (not shown) or otherwise have a non-circular cross-section. Biopsy probe assembly 938 in FIG. 24 includes an engagement tang 980 which extends vertically downward from the body of the biopsy probe assembly 938. Engagement tang 980 includes oppositely facing grooves 984 machined or otherwise formed in opposite side faces 982 of tang 980.

Probe mount 820 includes an opening 824 in a top surface of the mount 820 sized for receiving the engagement tang 980. Opening 824 can extend through the fully thickness of mount 820, or extend partially through mount 820. A pair of spring loaded ball assemblies 830 can be disposed in cylindrically shaped holes 828 extending from opposite side surfaces of mount 820, the holes 828 communicating with opening 824. The spring loaded ball assemblies 830 can include: a ball 832 sized and shaped to engage a groove 984 in tang 980; a biasing element, such as a spring 834 for urging ball 832 into engagement with groove 984; and a plug 836 or other suitable mechanism for securing the ball and spring in probe mount 820. Suitable spring and ball assemblies can be purchased commercially. A user can, with a single hand, grasp the probe assembly 938 and engage the probe assembly with the probe mount 820 by pushing the tang 980 downward into the opening 824 until the balls 832 of the mount engage the grooves 984 of the tang. The biasing force provided by the springs 834 assist in holding the biopsy probe assembly 938 in a fixed position with respect to the probe mount 820, and can reduce clearances that otherwise could result in positioning errors. The user can disengage the probe assembly 938 from the probe mount 820 with a single hand by pulling upwardly on the probe assembly 938 with sufficient force to overcome the spring force of the spring loaded ball assemblies. It will be understood that while a particular ball detent mechanism is shown for use in FIG. 24, other suitable release mechanisms may be substituted for releasably coupling the biopsy probe assembly to the biopsy probe mount.

Figure 25:
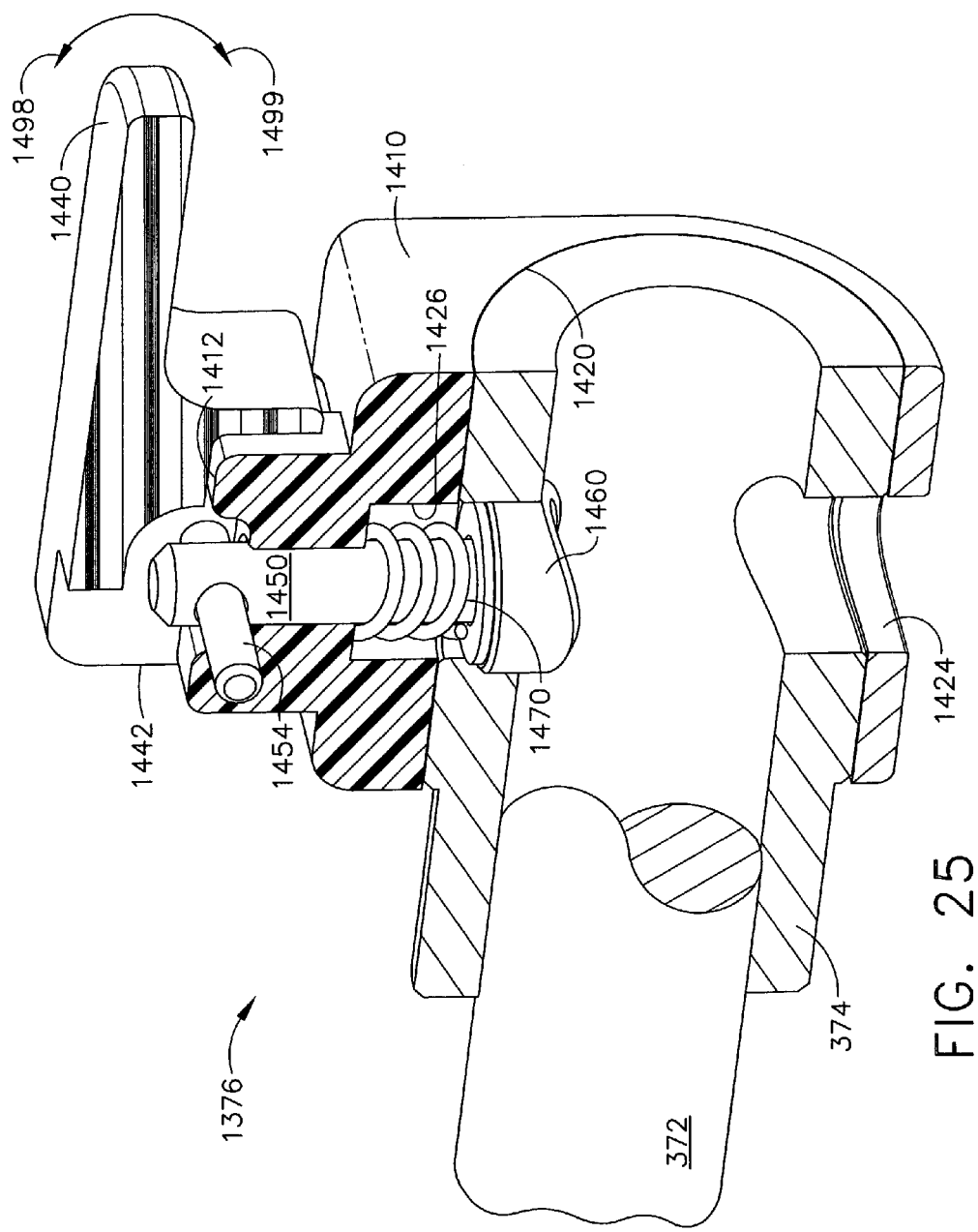
FIG. 25 is a cut away isometric view of a three position locking clamp.

FIG. 25 is an isometric cut-away illustration of a three piece clamp 1376 useful in the present invention. Clamp 1376 includes a housing body 1410, which can include a generally cylindrical through bore 1420 for receiving a bushing or other bearing member, such as a bushing 374, and a shaft, such as shaft 372. Body 1410 can also include a radially extending assembly access aperture 1424 which can communicate with bore 1420 through a hole in bushing 374. Clamp 1376 also includes a toggle lever 1440, a clamp actuation rod 1450, a pin 1454 extending through a hole in rod 1450 and through a clevis in lever 1440 to pivotably connect lever 1440 to rod 1450. The pin 1454 passes through rod 1450 near a top end of rod 1450, and a shaft engaging member, such as pad 1460 is attached to an opposite second end of rod 1450. The pad 1460 can extend through an cylindrically shaped whole in bearing 374. The pad 1460 can have a bottom surface shaped to accommodate a diameter of shaft 372 (e.g. a shape generated by the surface of intersection of two perpendicular cylinders), and the pad 1460 can be made a relatively soft, deformable material, such as rubber, a rubber like material, a deformable polymer, or other suitable material useful in frictionally engaging a shaft (e.g. shaft 372). A biasing member, such as a coil spring 1470 can be disposed in a recess 1426 in housing body 1410. Coil spring can be positioned around rod 1450 and can urge pad 1460 downward into engagement with shaft 372 when the lever 1440 is in the horizontal position shown in FIG. 25. This first horizontal position of lever 1440 corresponds to a shaft lock position. The lever 1440 can be rotated as indicated by arrowhead 1498) to a second position where the lever is generally vertically upright (see FIG. 26), such that rotation of the lever 1440 raises pin 1454 vertically, and so raises pad 1460 up out of engagement with shaft 372 to unlock shaft 372. Lever 1440 has a surface 1442 which abuts against a top surface of housing 1410 to maintain lever 1440 in the upright second position once lever 1440 has been rotated (counter-clockwise in FIG. 25) to that position. Surface 1442 can be spaced a distance from the axis 1454 so that when lever 1440 is rotated and surface 1442 is positioned to abut the housing 1410, the pin 1454 is raised with respect to the housing, thereby raising rod 1450 and pad 1460 against the biasing force of spring 1470. A third lever position corresponds to applying a downward pressing force on lever 1440, in a direction shown by arrowhead 1499. Pressing downward on lever 1440 causes lever 1440 to rock or pivot about a surface 1412 on housing 1410, thereby raising pin 1454 and rod 1450 to lift pad 1460 out of engagement with shaft 372.

Figure 26:
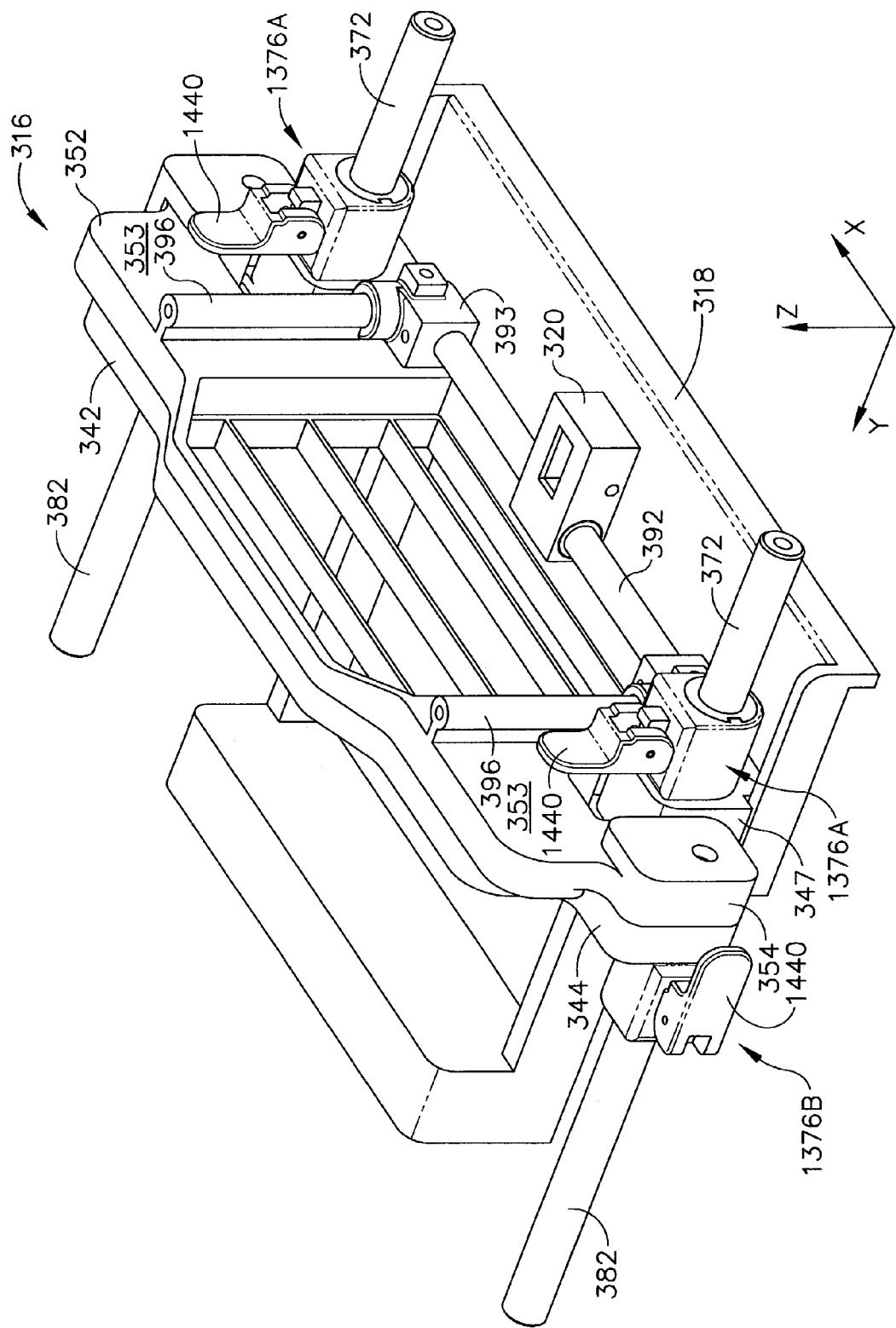
FIG. 26 is an isometric illustration of the localization mechanism of FIG. 22 illustrating sliding a compression plate along a Y axis for compressing tissue.
Figure 27:
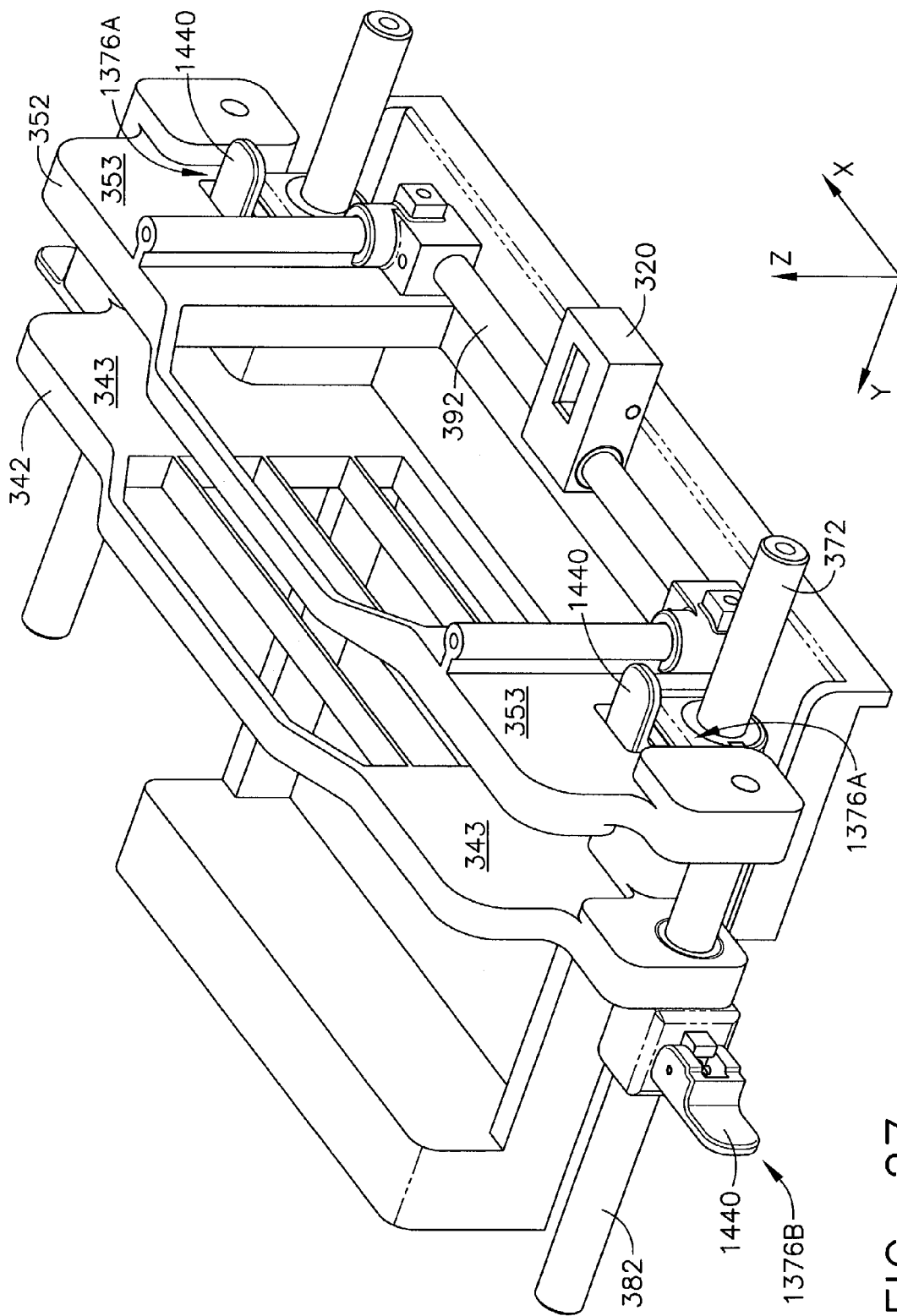
FIG. 27 is perspective illustration of the localization mechanism of FIG. 22 showing a compression plate locked into position upon movement of a biopsy probe support plate relative to the compression plate along the Y axis.

FIGS. 26 and 27 are perspective illustrations showing use of the three position clamp 1376 with the fixture assembly 316 shown in FIG. 22. In FIG. 26, the fixture assembly 316 is shown prior to attaching the biopsy probe assembly to probe mount 320. FIG. 26 shows clamps 1376B in a locked (first) position and clamps 1376A in an unlocked (second) position. With clamps 1376B in the locked position, compression plate 342 and biopsy probe support plate 352 can be pushed together toward breast tissue (not shown) to compress the breast. In FIG. 26, upright levers 1440 of clamps 1376A extend above (along Z direction) a lower portion of the side portions 353 of plate 352.

Once the beast compression plate 342 is in position, compressing tissue, it is desirable to lock the position of plate 342 and then move plate 352 back, away from plate 342 along the Y axis so that a biopsy probe device can be attached to probe mount 320. FIG. 27 shows locking clamps 1376B with levers 1440 in an unlocked (second) position so that shaft 382 and plate 352 (to which shaft 382 is attached) can slide along the Y axis away from compression plate 342. FIG. 27 also illustrates how movement of plate 352 relative to plate 342 automatically locks compression plate 342 relative to shaft 372 (and so fixes plate 342 against breast tissue). In FIG. 27, movement of plate 352 relative to plate 342 causes plate side portion 353 to engage upstanding levers 1440 locking clamps 1376A, forcing rotation of levers 1440 to the locked (first) position, and thereby locking the Y position of plate 342 on shafts 372. Accordingly, even if the physician or other user of the device forgets to lock the Y position of the compression plate prior to loading the biopsy device, the fixture of FIG. 27 will automatically lock the position of the compression plate upon retraction of the biopsy probe support plate 352. Once the plate 352 has been moved back along the Y axis relative to the compression plate 342, the biopsy probe assembly 438 can be attached to the probe mount 320.

While the present invention has been illustrated by description of several embodiments and while the illustrative embodiments have been described in considerable detail, it is not the intention of the applicant to restrict or in any way limit the scope of the appended claims to such detail. For example, although a localization mechanism 316/516 is depicted that laterally compresses a downward hanging breast, aspects of the present invention are applicable to other orientations of localization/fixturing and imaging.

Additionally, while two shafts 372/572 are shown in FIGS. 22 and 23, it may be desirable in other embodiments to have a single shaft 372 (or 572), such as a shaft mounted to the side of, or centered with respect to, plates 342 and 352.

As an additional example, although MRI is discussed herein as the imaging modality for stereotopically guiding the core biopsy, the invention may apply to other imaging modes.

As a further example, although a Cartesian XYZ positioning approach is disclosed herein, a polar or spherical positioning approach may be implemented in whole or in part so that the detachable probe assembly enters at a predefined angle.

As another example, although a prone breast compression device is depicted, application of the present invention may be used in medical devices oriented in other manners, to include standing, lying on one side, or supine. In addition, aspects of the present invention may be applicable to positioning a biopsy probe through a medial compression plate, or a top and bottom compression plate pair, instead of a lateral compression plate. Furthermore, aspects of the present invention are applicable to other diagnostic imaging modalities currently used or that become available in the future. In addition, aspects of the present invention would have application to diagnostic guided biopsy procedures on other portions of the body, as well as to positioning a probe for utilizing other diagnostic and treatment devices in a minimally invasive manner.

What is claimed is:

1. An apparatus for use in positioning a biopsy device, comprising:

a first pair of generally parallel, spaced apart elongated supports extending in a Y direction;

a second pair of generally parallel, spaced apart elongated supports extending in a Z direction perpendicular to the Y direction;

a probe support plate supported for movement in the Y direction, the probe support plate having at least one opening therethrough through which a portion of a biopsy device can extend;

a mount for releasably engaging a biopsy device, the mount supported on the probe support plate to permit movement of the mount with respect to the support plate, the mount selectively positionable along a mount elongated support extending in an X direction perpendicular to the Y and Z directions; and a breast compression member supported for movement in the Y direction and positionable in spaced relationship from the probe support plate, the breast compression member extending along at least two of the X, Y, or Z directions;

wherein the second pair of generally parallel, spaced apart supports is selectively positionable in the Y direction along the first pair of generally parallel, spaced apart elongated supports, and wherein the mount elongated support is selectively positionable in the Z direction along the second pair of generally parallel, spaced apart elongated supports, such that the mount for releasably engaging a biopsy device is selectively positionable along each of the X, Y, and Z directions.

2. The apparatus of claim 1 further comprising means for looking the position of the mount relative to the first pair of generally parallel, spaced apart elongated supports.

3. The apparatus of claim 1 wherein the Z direction corresponds to the vertical direction.

* * * * *